United States Patent
Dilhas et al.

(10) Patent No.: US 9,994,545 B2
(45) Date of Patent: Jun. 12, 2018

(54) CRYSTALLINE FORMS OF AN ANDROGEN RECEPTOR MODULATOR

(71) Applicants: Aragon Pharmaceuticals, Inc., San Diego, CA (US); Sloan-Kettering Institute For Cancer Research, New York, NY (US)

(72) Inventors: Anna Dilhas, Basel (CH); Mark R. Herbert, San Diego, CA (US); Ouathek Ouerfelli, New York, NY (US); Nicholas D. Smith, San Diego, CA (US)

(73) Assignees: Aragon Pharmaceuticals, Inc., San Diego, CA (US); Sloan-Kettering Institute For Cancer Research, New York, NY (US)

( * ) Notice: Subject to any disclaimer, the term of this patent is extended or adjusted under 35 U.S.C. 154(b) by 0 days. days.

(21) Appl. No.: 15/262,522

(22) Filed: Sep. 12, 2016

(65) Prior Publication Data
US 2017/0001977 A1  Jan. 5, 2017

Related U.S. Application Data

(62) Division of application No. 14/406,520, filed as application No. PCT/US2013/044116 on Jun. 4, 2013, now Pat. No. 9,481,663.

(60) Provisional application No. 61/656,888, filed on Jun. 7, 2012.

(51) Int. Cl.
C07D 401/04 (2006.01)

(52) U.S. Cl.
CPC .................. *C07D 401/04* (2013.01)

(58) Field of Classification Search
CPC .................................. C07D 401/04
USPC ........................... 546/15; 514/278
See application file for complete search history.

(56) References Cited

U.S. PATENT DOCUMENTS

| 8,445,507 B2 | 5/2013 | Jung et al. |
| 8,461,343 B2 | 6/2013 | Ouerfelli et al. |
| 2007/0004753 A1 | 1/2007 | Sawyers et al. |
| 2014/0309262 A1 | 10/2014 | Jung et al. |

FOREIGN PATENT DOCUMENTS

| CN | 101032483 A | 9/2007 |
| CN | 101454002 A | 6/2009 |
| WO | WO 2007/126765 | 11/2007 |
| WO | WO 2007/127010 | 11/2007 |
| WO | WO 2008/119015 | 10/2008 |
| WO | WO 2011/103202 A2 | 8/2011 |
| WO | WO 2013/184681 A1 | 12/2013 |

OTHER PUBLICATIONS

Vippagunta et al., "Crystalline solids", Advanced Drug Delivery Reviews 48 (2001) 3-26.*
Bernstein, "Polymorphism in . . . " p. 115-118, 272 (2002).*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Kirk-Othmer "Crystallization" Encyclopedia of Chem. Tech. v. 8, p. 95-147 (2002).*
Seddon, "Pseudopolymorph, etc.," Crystal Growth & Design. 4(6), 1087 (2004 (2 pages from internet).*
Chen et al., "Molecular determinants of resistance to antiandrogen therapy", Nature Medicine, Jan. 2004, 10, 33-39.
Chen, "Hygroscopicity of Pharmaceutical Crystals", A Dissertation submitted to the faculty of Graduate School of The University of Minnesota, Jan. 2009, 315 pages.
Clegg et al., "ARN-509: A Novel Antiandrogen for Prostate Cancer Treatment", Cancer Research, Mar. 2012, Issue 72, No. 6, 1494-1503.
Jung et al., "Structure-Activity Relationship for Thiohydantoin Androgen Receptor Antagonists for Castration-Resistant Prostate Cancer (CRPC)," Journal of Medicinal Chemistry, Apr. 2010, vol. 53, No. 7, 2779-2796.
Singhal et al., "Drug polymorphism and dosage form design: a practical perspective", Advanced Drug Delivery Reviews, 2004, 56, 335-347.
Yoshino et al., "Design and synthesis of an androgen receptor pure antagonist (CH5137291) for the treatment of castration-resistant prostate cancer", Bioorganic & Medicinal Chemistry, Dec. 2010, vol. 18, No. 23, 8150-8157.

* cited by examiner

*Primary Examiner* — Patricia L Morris
(74) *Attorney, Agent, or Firm* — Baker & Hostetler LLP

(57) ABSTRACT

Described herein are amorphous and crystalline forms of the androgen receptor modulator 4-[7-(6-cyano-5-trifluoromethylpyridin-3-yl)-8-oxo-6-thioxo-5,7-diazaspiro[3.4]oct-5-yl]-2-fluoro-N-methylbenzamide. Also described are pharmaceutical compositions suitable for administration to a mammal that include the androgen receptor modulator, and methods of using the androgen receptor modulator, alone and in combination with other compounds, for treating diseases or conditions that are associated with androgen receptor activity.

21 Claims, 19 Drawing Sheets

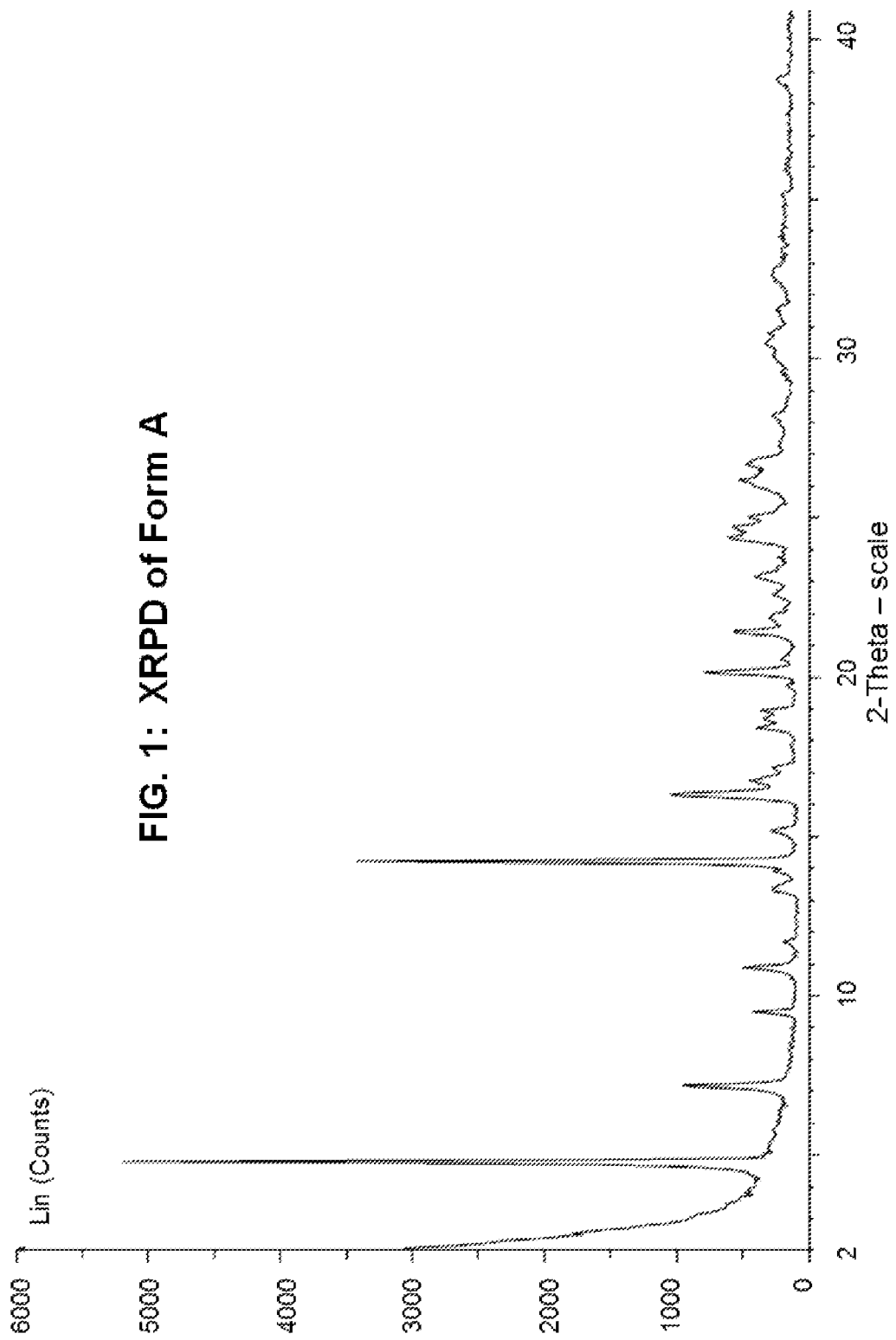
FIG. 1: XRPD of Form A

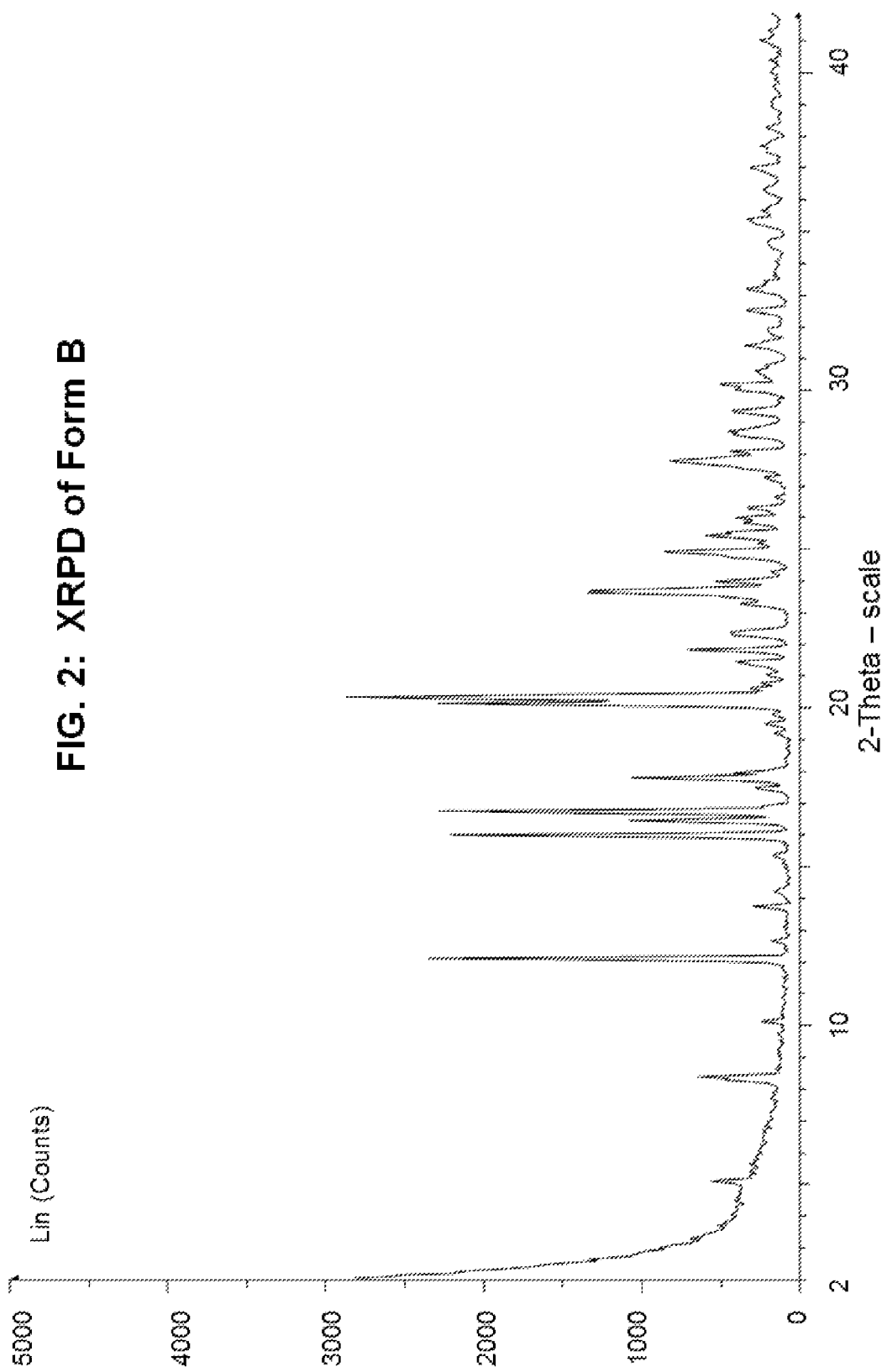
FIG. 2: XRPD of Form B

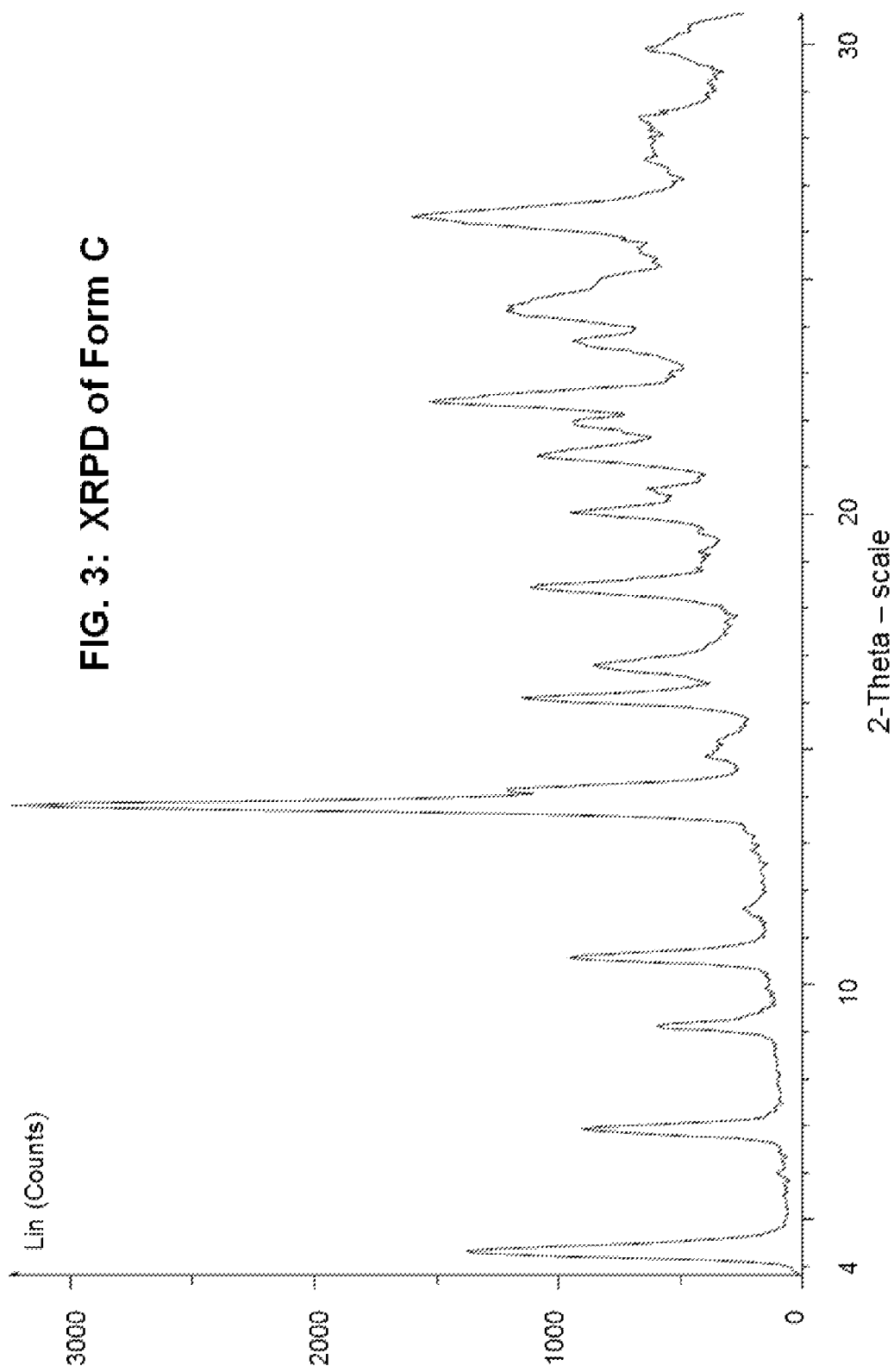

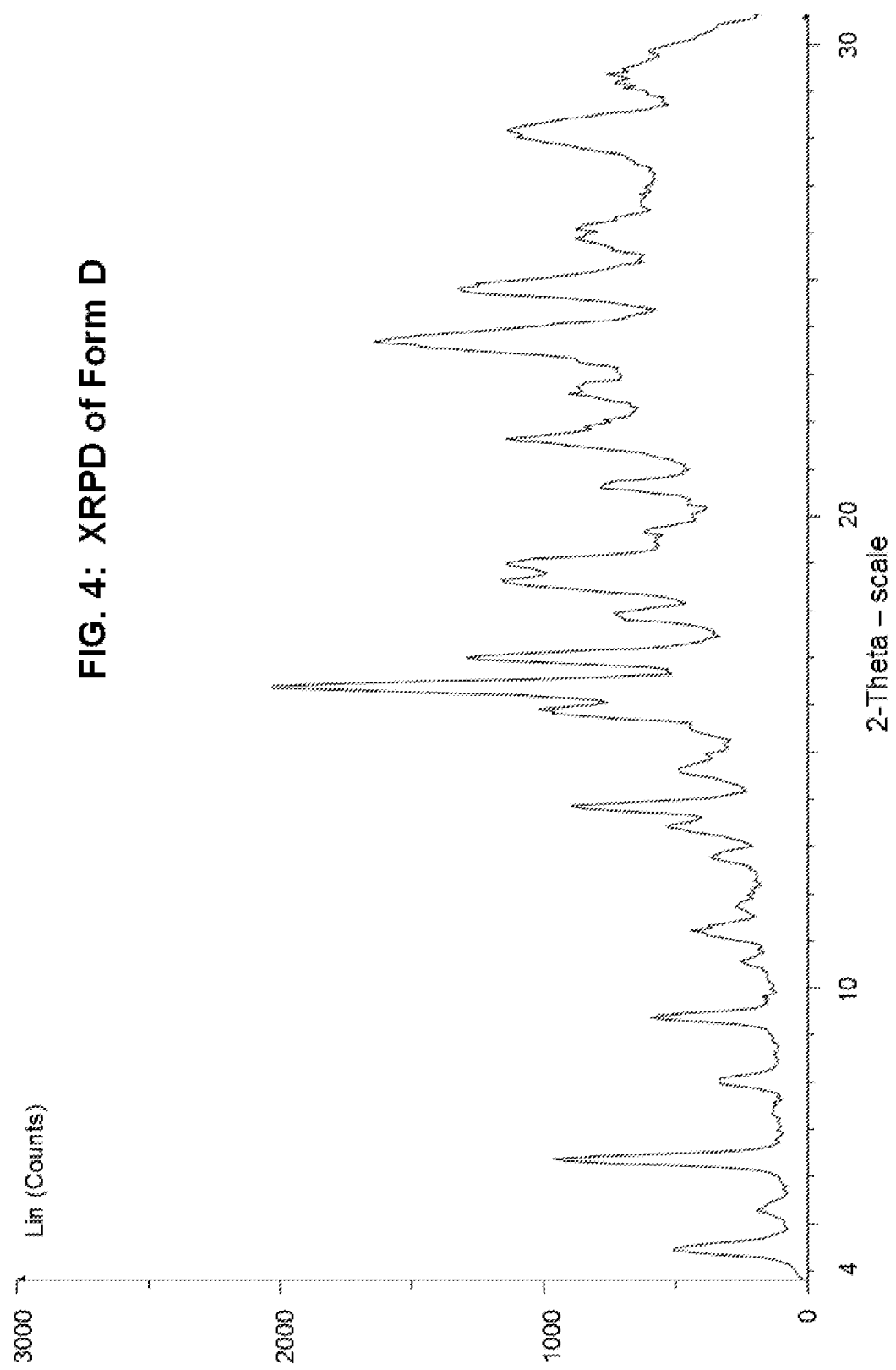
FIG. 4: XRPD of Form D

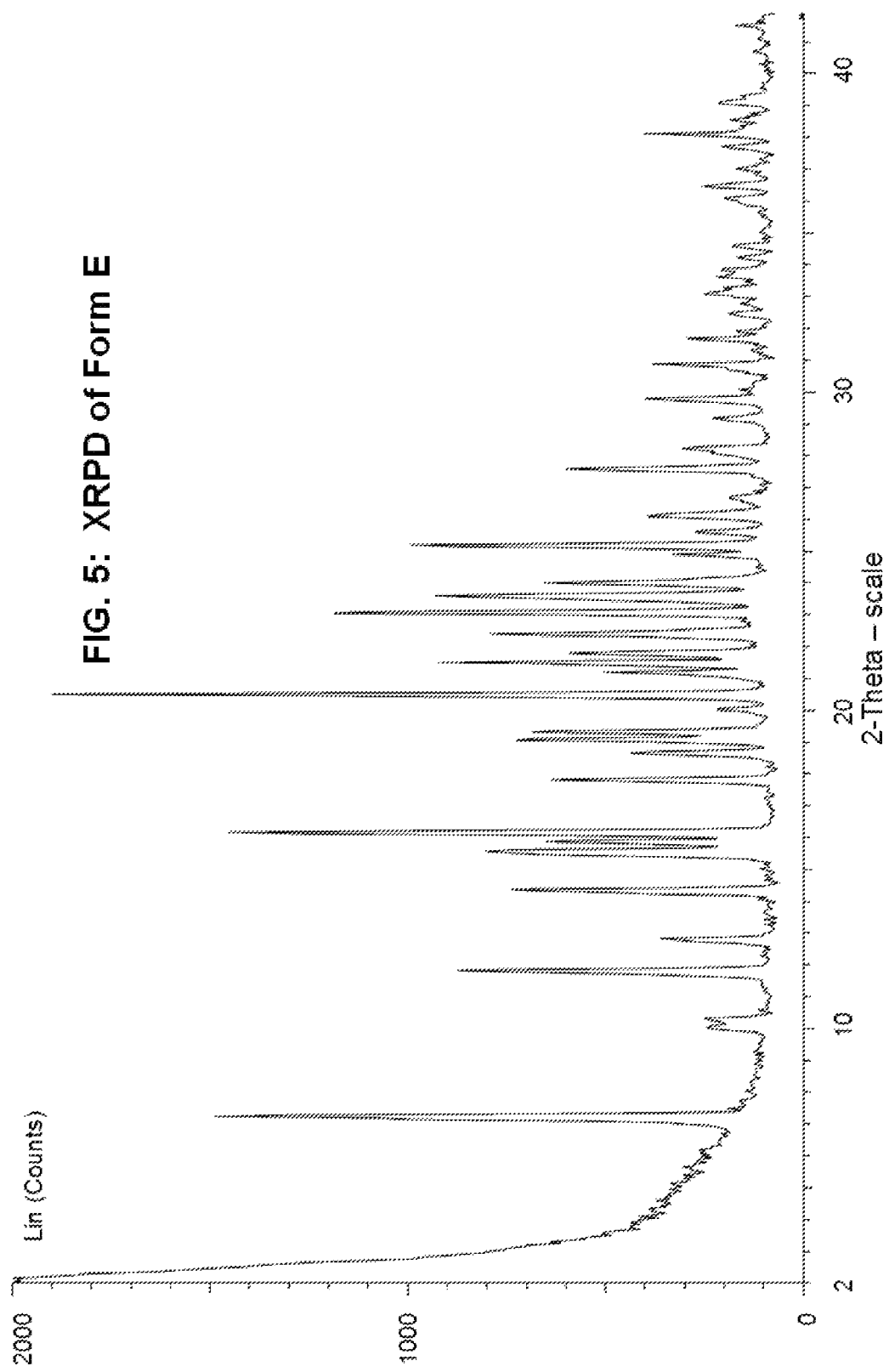

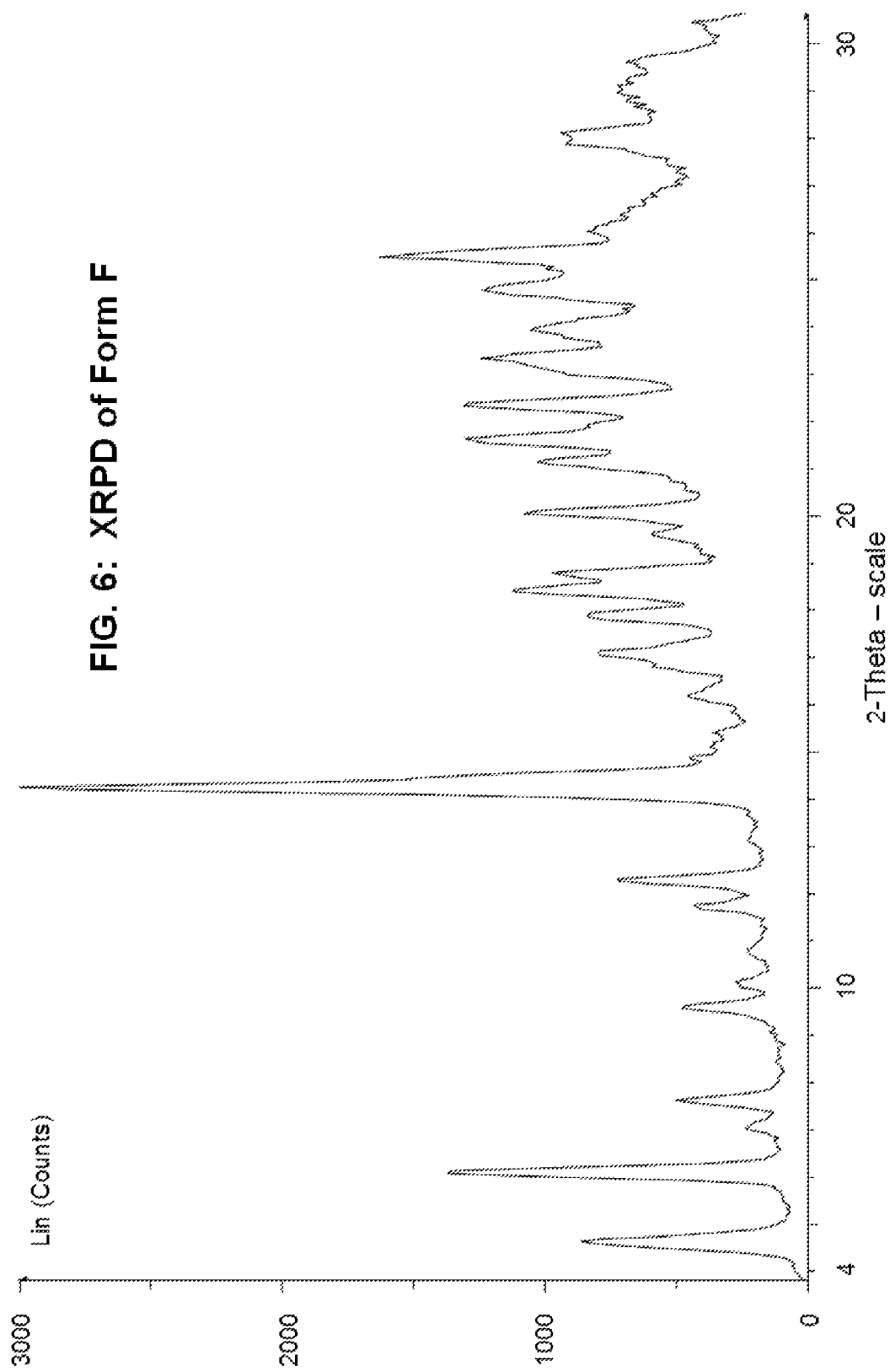
FIG. 6: XRPD of Form F

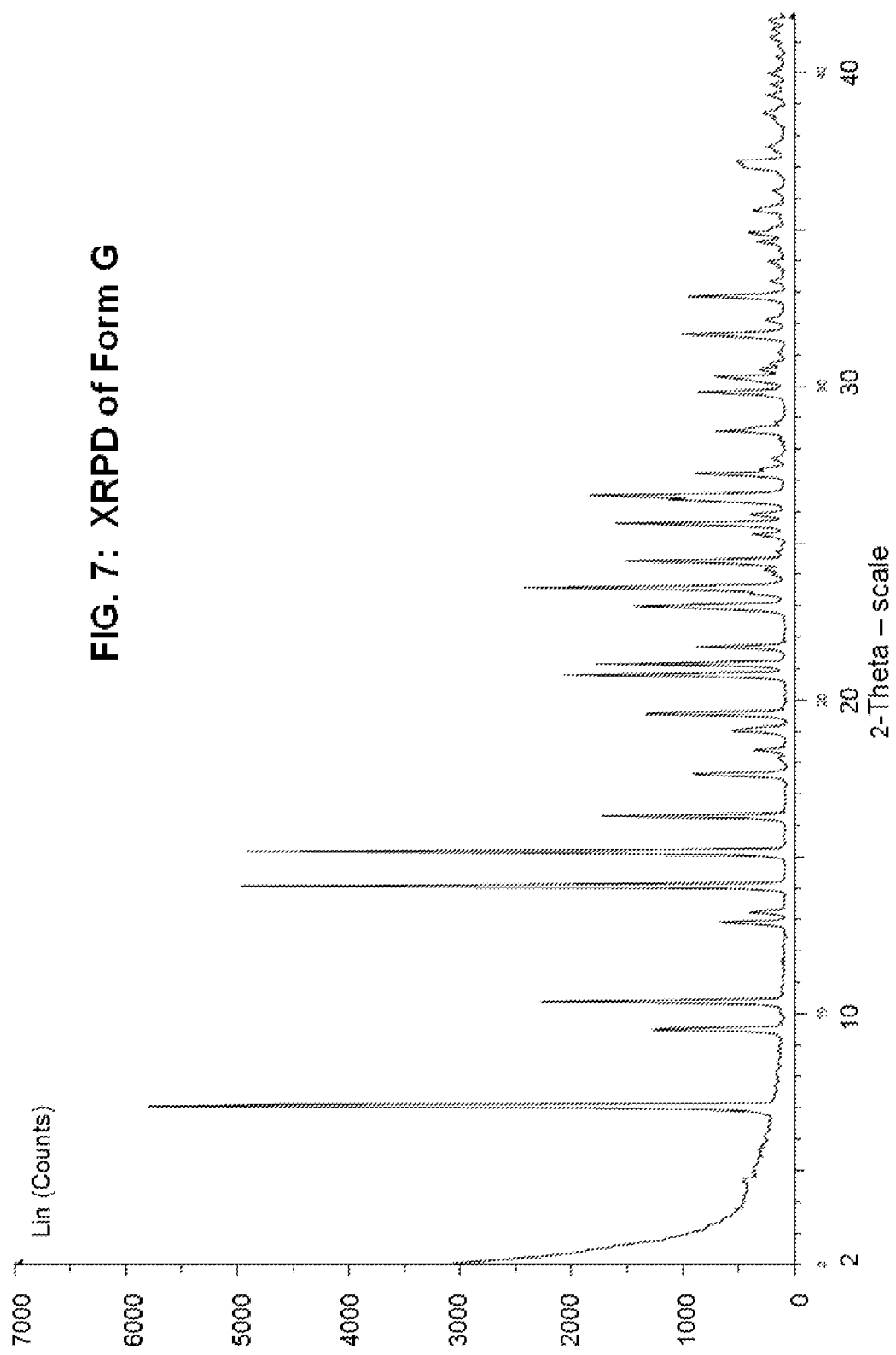
FIG. 7: XRPD of Form G

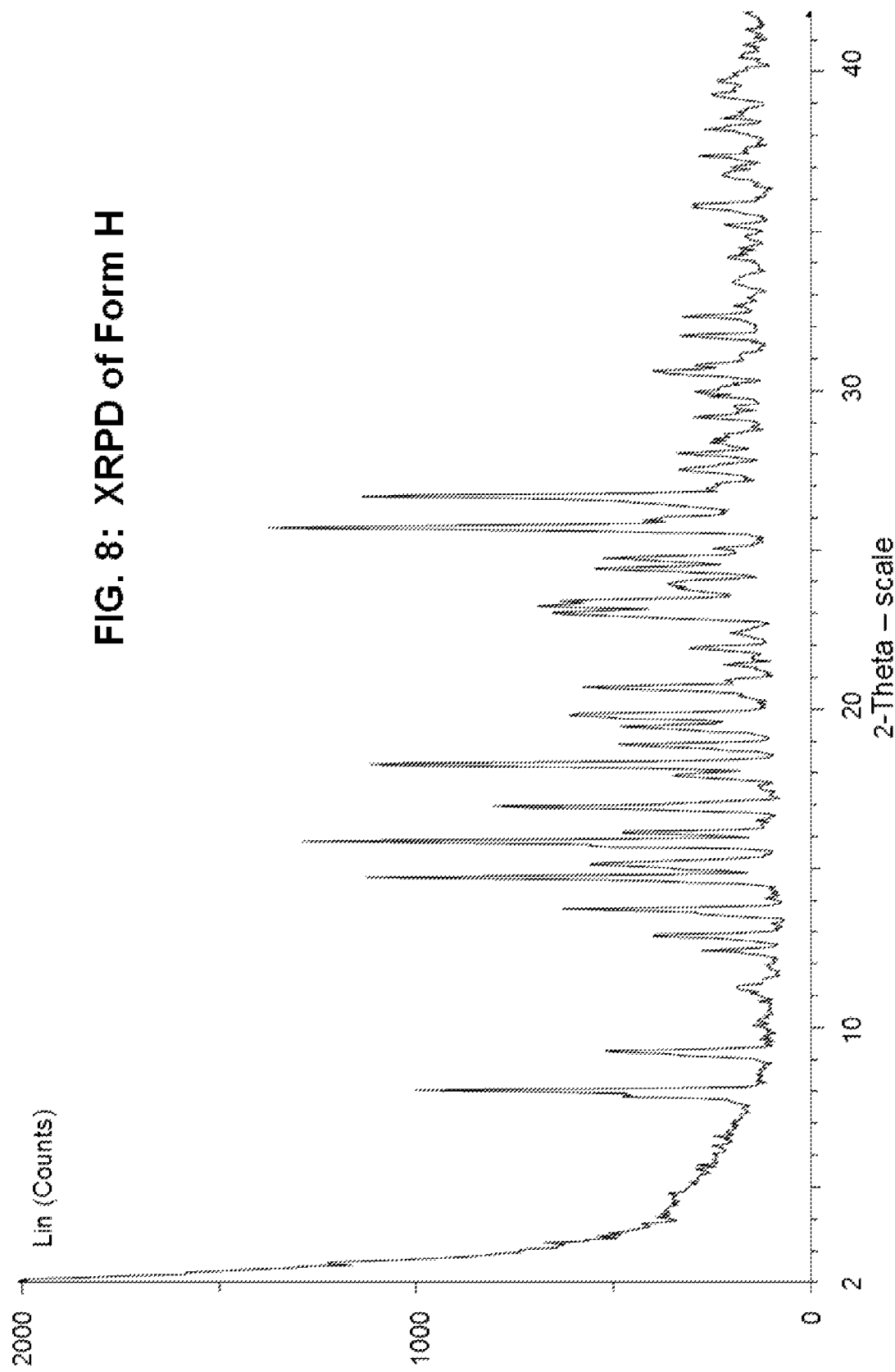

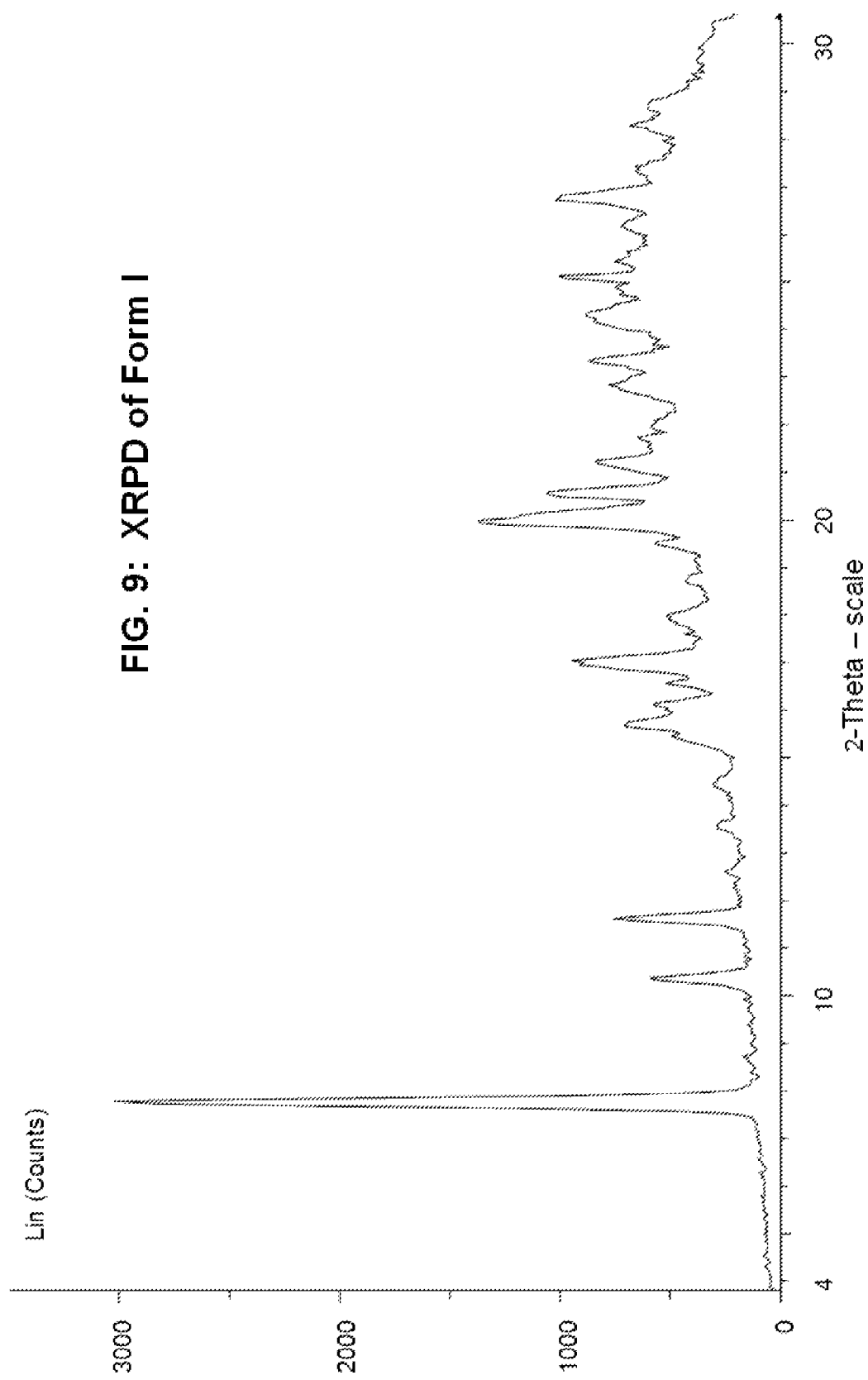

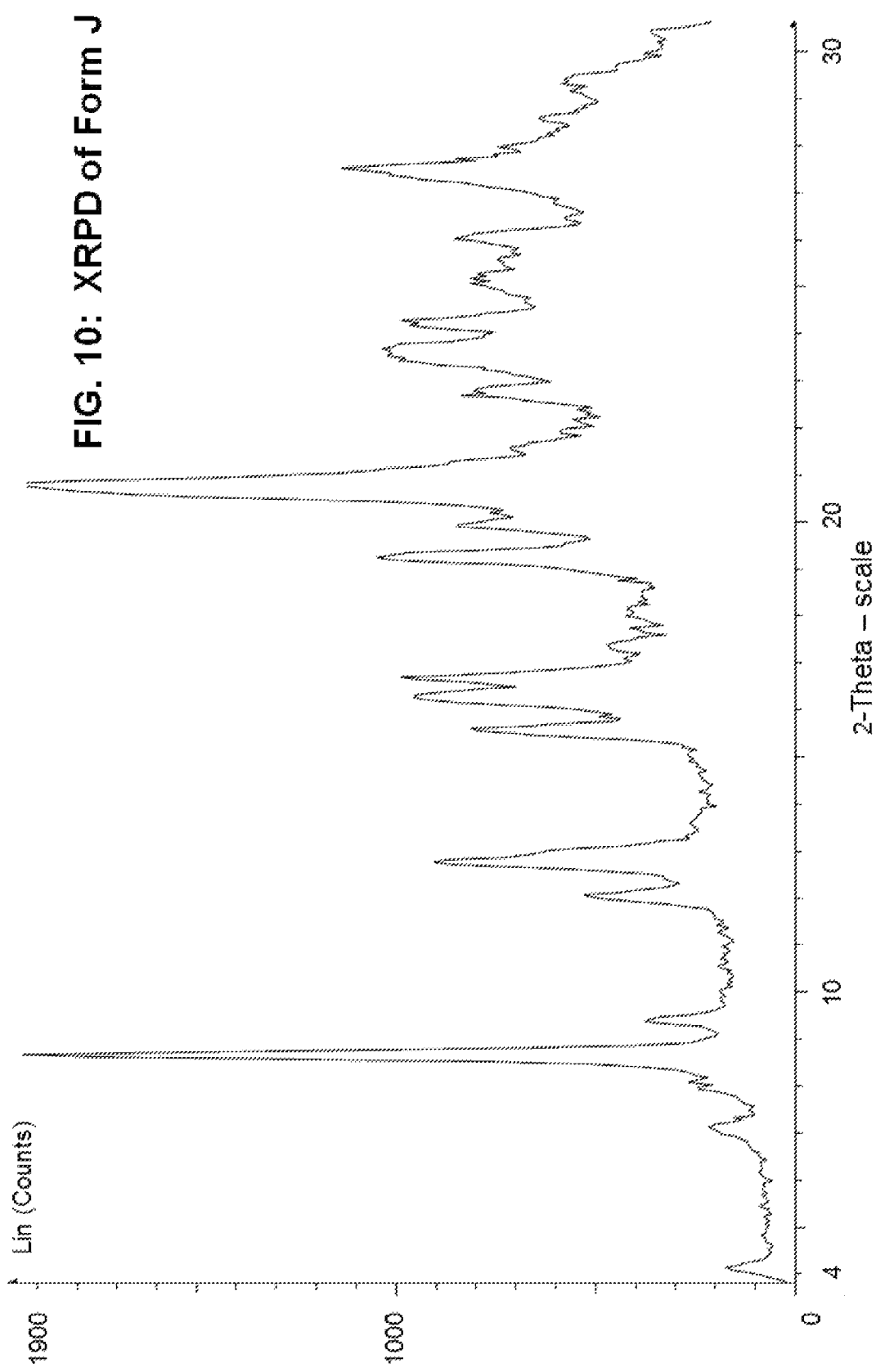

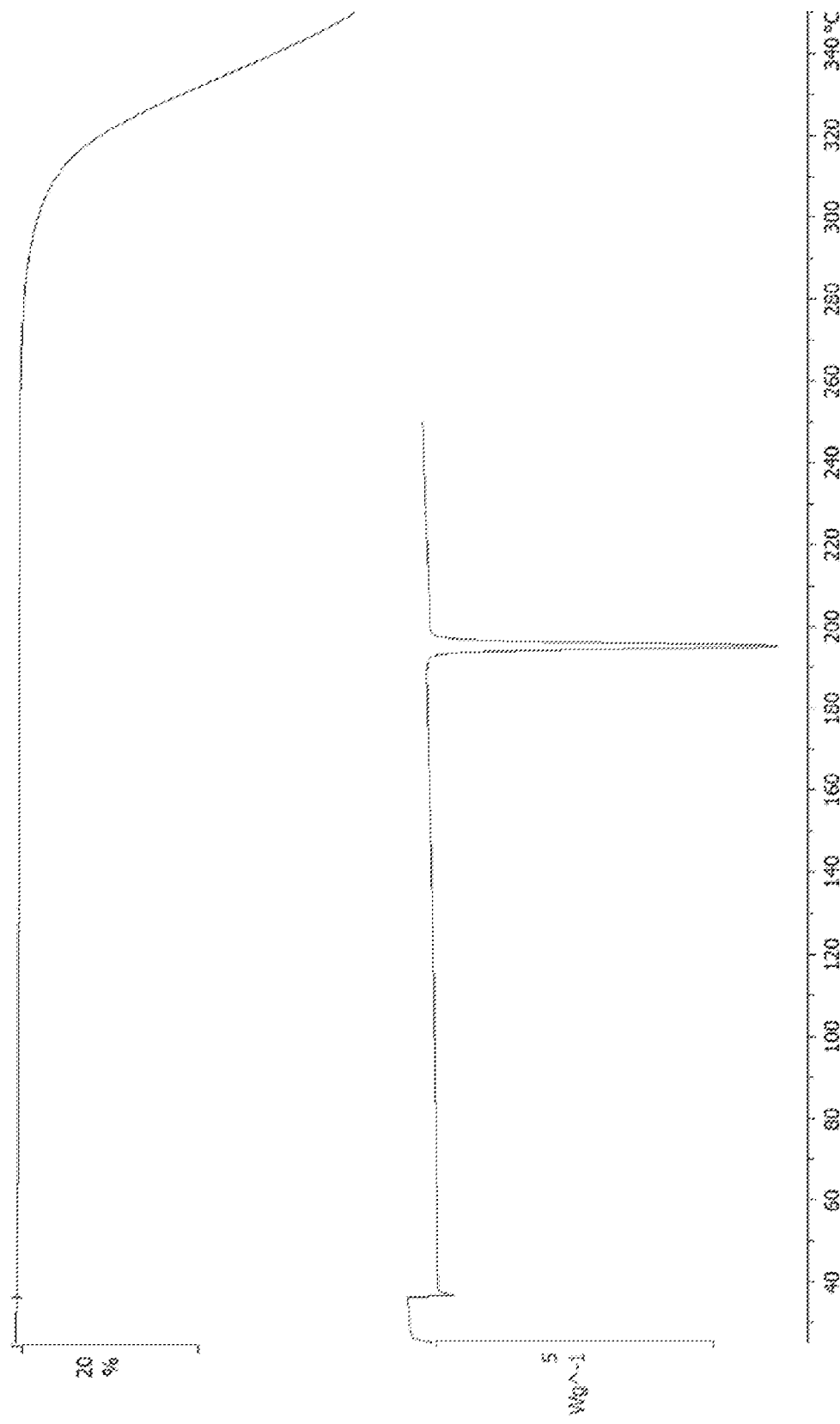
FIG. 11: TGA and DSC Thermograms of Form B

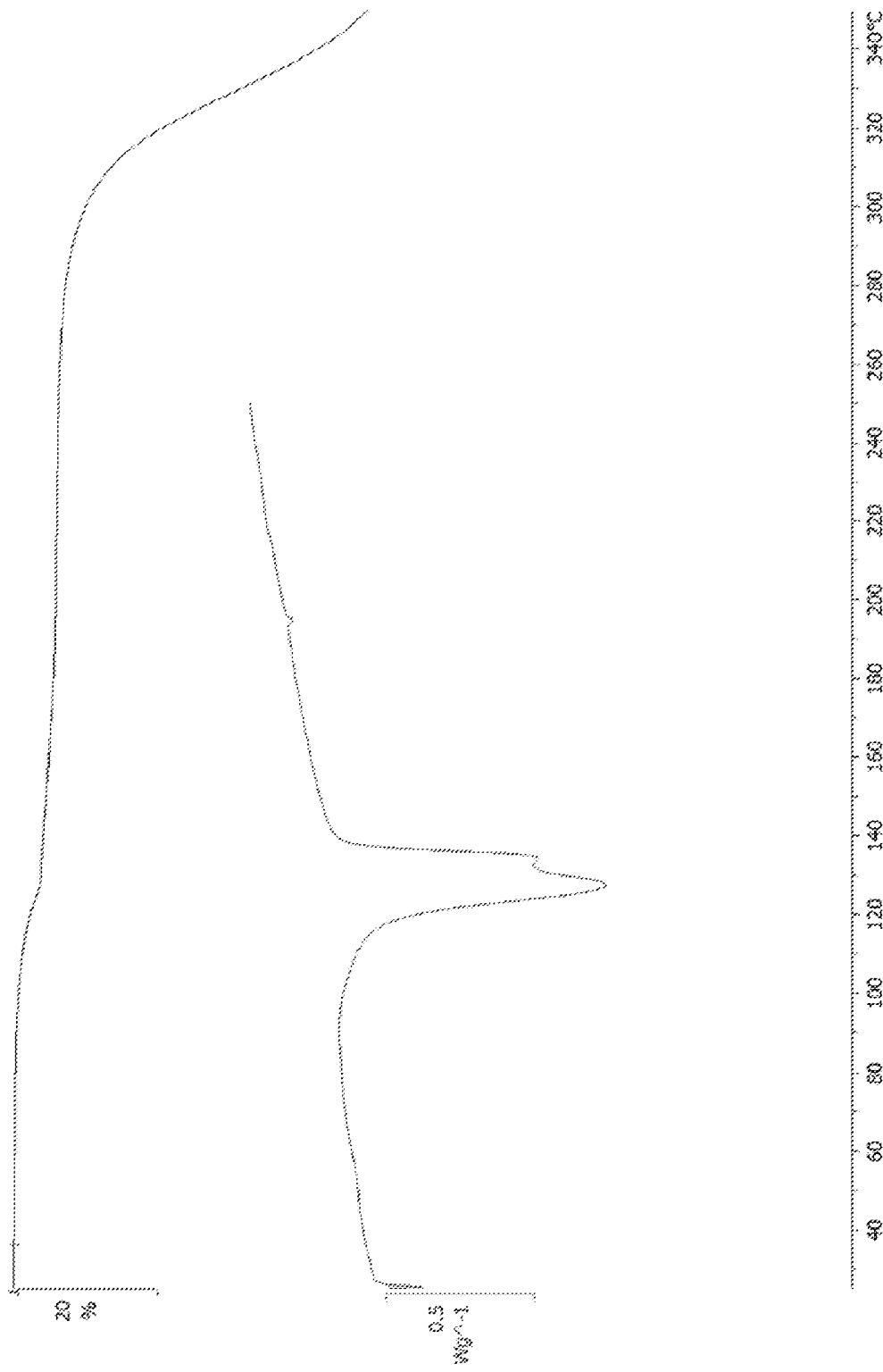
FIG. 12: TGA and DSC Thermograms of Form C

FIG. 13: TGA and DSC Thermograms of Form D

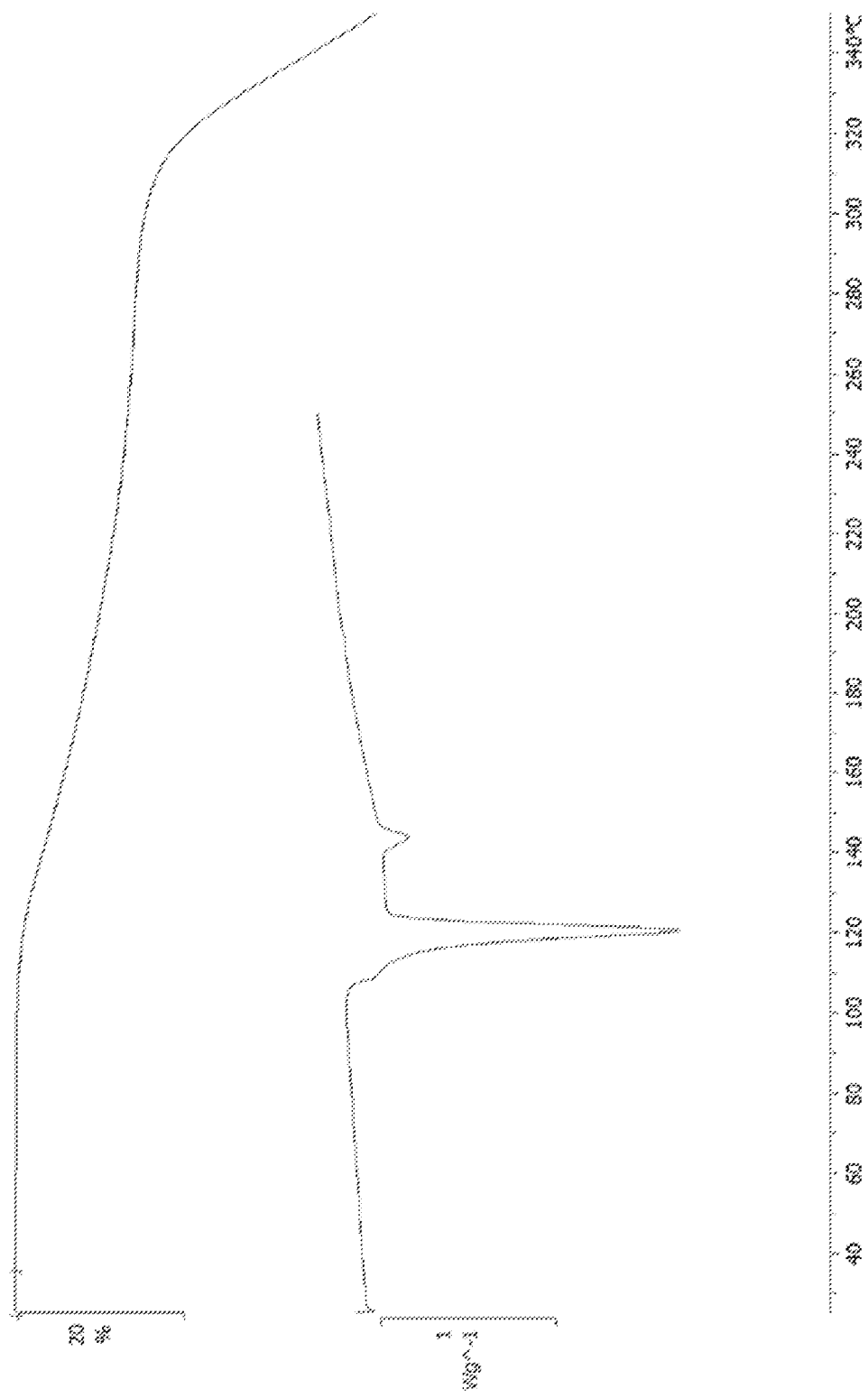
FIG. 14: TGA and DSC Thermograms of Form E

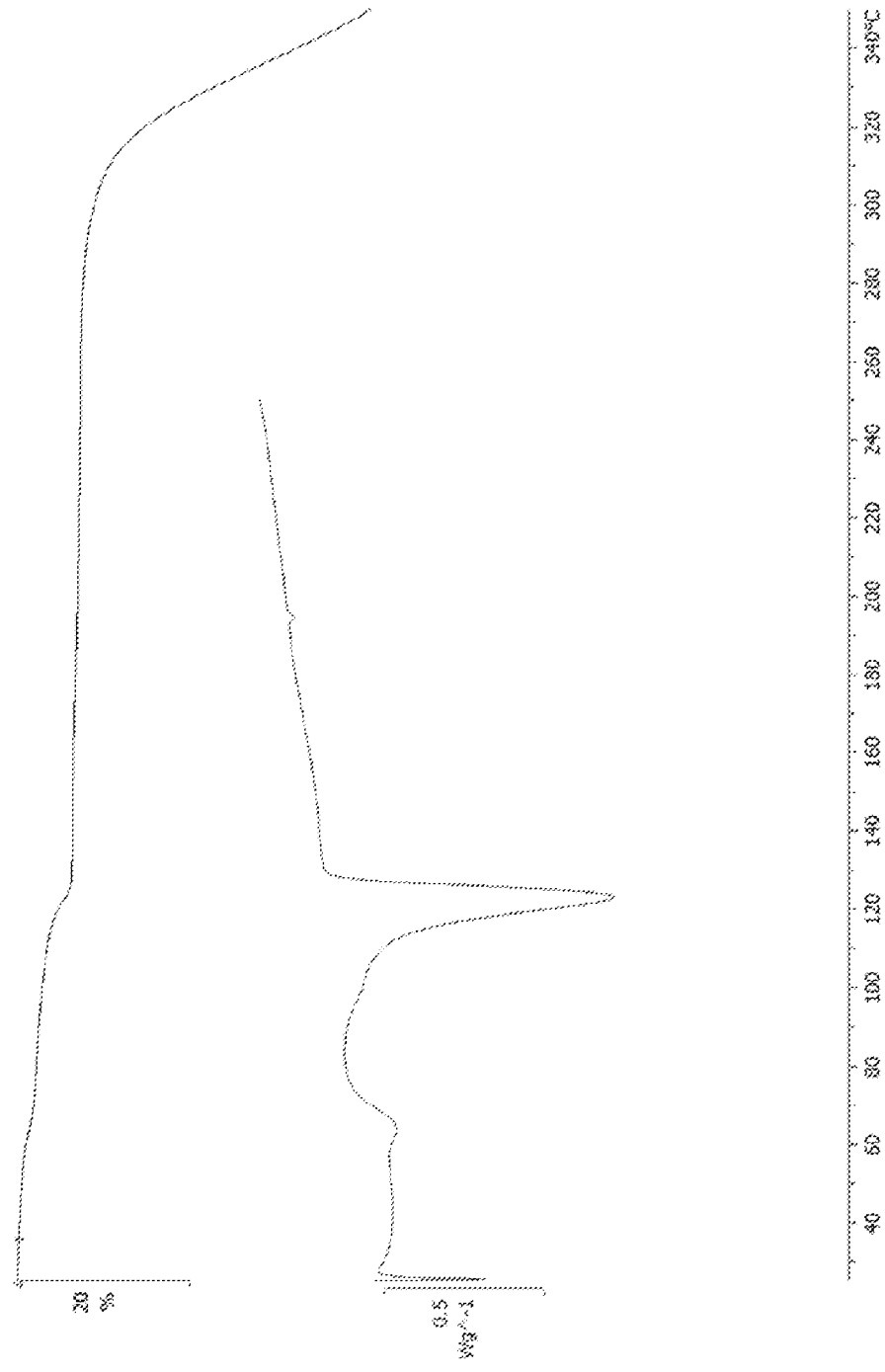
FIG. 15: TGA and DSC Thermograms of Form F

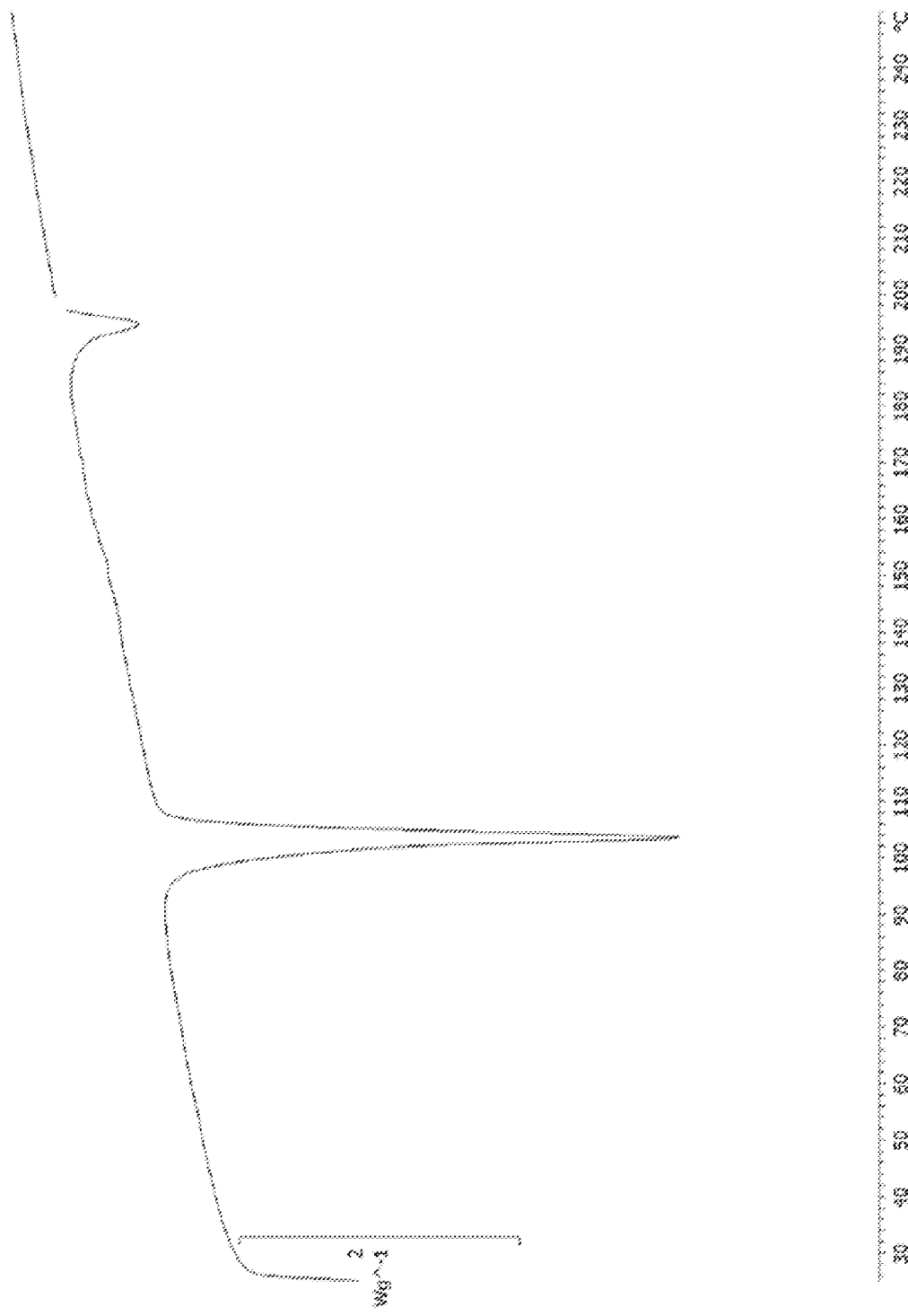
FIG. 16: TGA and DSC Thermograms of Form G

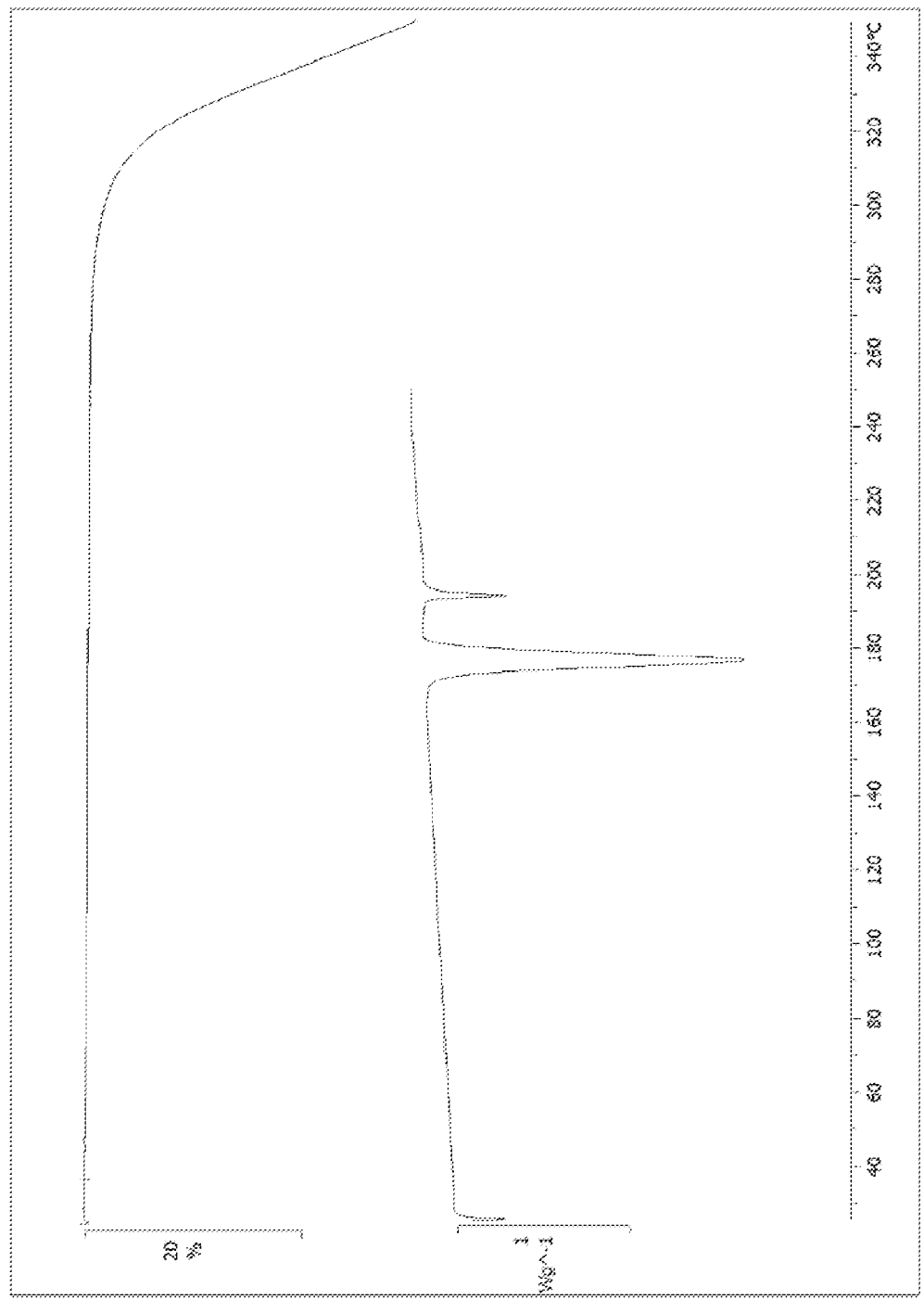
FIG. 17: TGA and DSC Thermograms of Form H

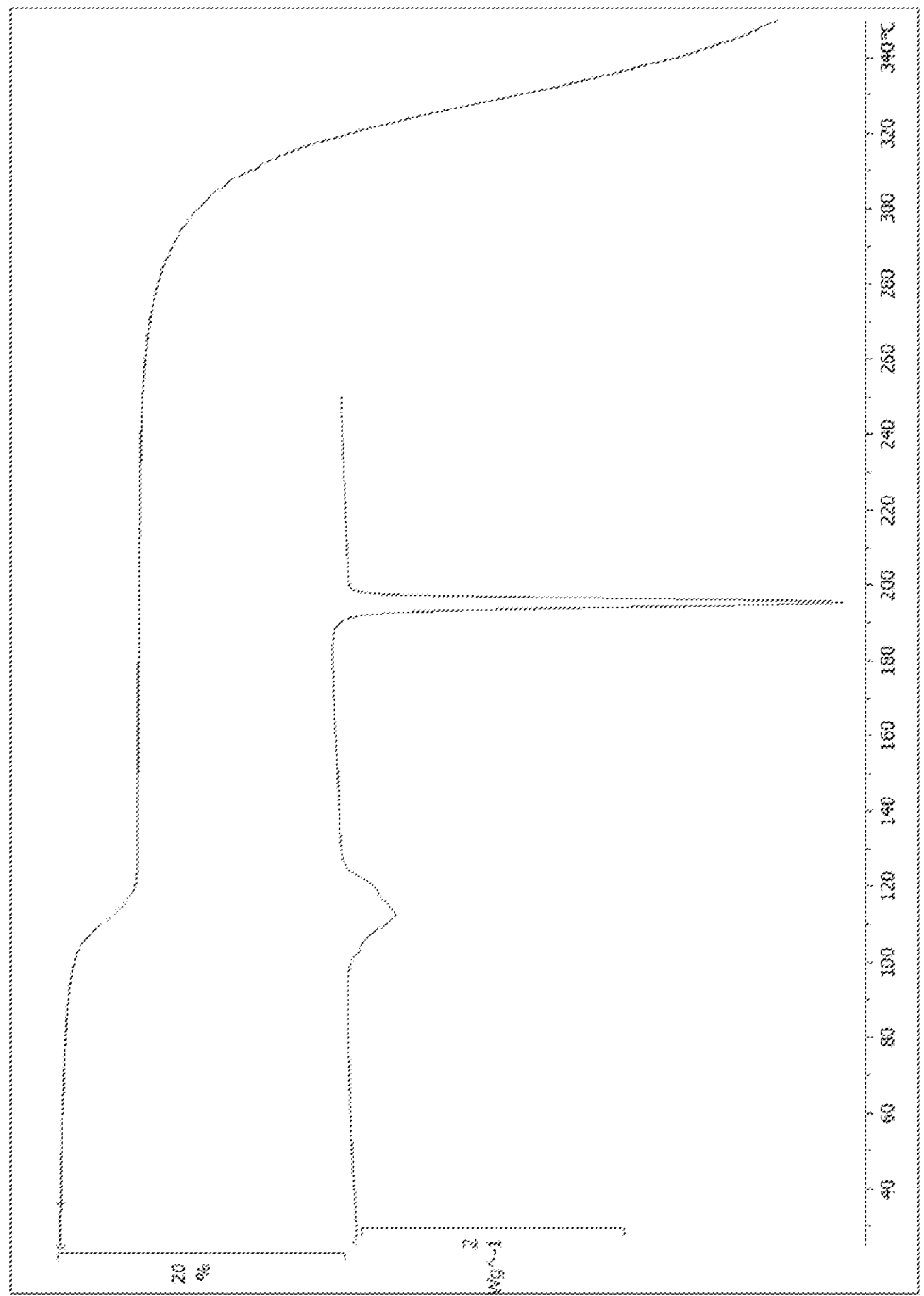
FIG. 18: TGA and DSC Thermograms of Form J

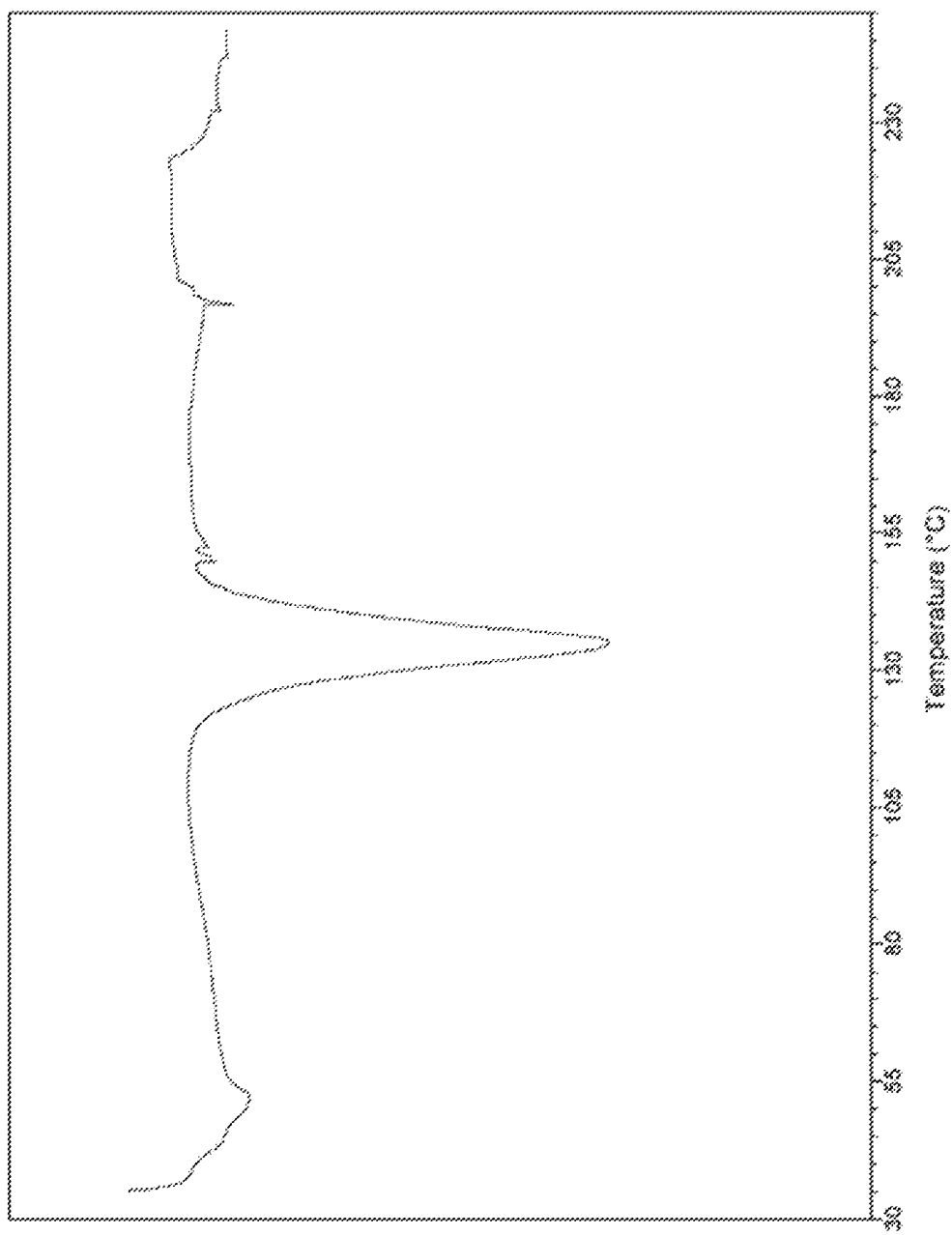
FIG. 19: DSC Thermogram of Form A

CRYSTALLINE FORMS OF AN ANDROGEN RECEPTOR MODULATOR

RELATED APPLICATIONS

This application is a divisional application of U.S. patent application Ser. No. 14/406,520, filed Dec. 8, 2014, which claims priority to, and is a U.S. National Stage Application of PCT/US2013/044116, filed Jun. 4, 2013, which claims the benefit of U.S. Provisional Patent Application Ser. No. 61/656,888 entitled "CRYSTALLINE FORMS OF AN ANDROGEN RECEPTOR MODULATOR" filed on Jun. 7, 2012, each of which is herein incorporated by reference in its entirety.

FIELD OF THE INVENTION

Described herein are crystalline forms of the androgen receptor modulator 4-[7-(6-cyano-5-trifluoromethylpyridin-3-yl)-8-oxo-6-thioxo-5,7-diazaspiro[3.4]oct-5-yl]-2-fluoro-N-methylbenzamide, pharmaceutically acceptable salts, solvates, as well as pharmaceutical compositions thereof, and methods of use thereof in the treatment or prevention of diseases or conditions associated with androgen receptor activity.

BACKGROUND OF THE INVENTION

The androgen receptor ("AR") is a ligand-activated transcriptional regulatory protein that mediates induction of a variety of biological effects through its interaction with endogenous androgens. Endogenous androgens include steroids such as testosterone and dihydrotestosterone. Testosterone is converted to dihydrotestosterone by the enzyme 5 alpha-reductase in many tissues.

The actions of androgens with androgen receptors have been implicated in a number of diseases or conditions, such as androgen dependent cancers, virilization in women, and acne, among others. Compounds that diminish the effects of androgens with androgen receptors and/or lower the concentrations of androgen receptors find use in the treatment of diseases or conditions in which androgen receptors play a role.

SUMMARY OF THE INVENTION

Described herein is 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, including all pharmaceutically acceptable solvates (including hydrates), polymorphs, and amorphous phases thereof, and methods of uses thereof. 4-[7-(6-Cyano-5-trifluoromethylpyridin-3-yl)-8-oxo-6-thioxo-5,7-diazaspiro[3.4]oct-5-yl]-2-fluoro-N-methylbenzamide, as well as pharmaceutically acceptable salts thereof, is used in the manufacture of medicaments for the treatment or prevention of diseases, disorders, or conditions associated with androgen receptor activity.

Described herein are pharmaceutical compositions comprising 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof as the active ingredient in the pharmaceutical composition.

In one aspect, described herein is crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form A. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form B. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form C. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form D. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form E. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form F. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form G. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form H. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form I. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is Form J.

In some embodiments, described herein is a pharmaceutically acceptable salt of 4-[7-(6-cyano-5-trifluoromethylpyridin-3-yl)-8-oxo-6-thioxo-5,7-diazaspiro[3.4]oct-5-yl]-2-fluoro-N-methylbenzamide, wherein the pharmaceutically acceptable salt is an acid addition salt. In some embodiments, the pharmaceutically acceptable salt is amorphous. In some embodiments, the pharmaceutically acceptable salt is crystalline.

In some embodiments, described herein is a pharmaceutical composition comprising a crystalline form of 4-[7-(6-cyano-5-trifluoromethylpyridin-3-yl)-8-oxo-6-thioxo-5,7-diazaspiro[3.4]oct-5-yl]-2-fluoro-N-methylbenzamide as described herein, and at least one additional ingredient selected from pharmaceutically acceptable carriers, diluents and excipients. In some embodiments, the pharmaceutical composition includes Form A of 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the pharmaceutical composition includes Form B. In some embodiments, the pharmaceutical composition includes Form C. In some embodiments, the pharmaceutical composition includes Form D. In some embodiments, the pharmaceutical composition includes Form E. In some embodiments, the pharmaceutical composition includes Form F. In some embodiments, the pharmaceutical composition includes Form G. In some embodiments, the pharmaceutical compositions includes Form H. In some embodiments, the pharmaceutical composition includes Form I. In some embodiments, the pharmaceutical composition includes Form J. In some embodiments, the pharmaceutical composition is in a form suitable for oral administration to a mammal. In some embodiments, the pharmaceutical composition is in an oral dosage form. In some embodiments, the pharmaceutical composition is in an oral solid dosage form. In some embodiments, the pharmaceutical composition is in the form of a tablet, pill, or capsule. In some embodiments, the pharmaceutical composition is in the form of a capsule. In some embodiments, the pharmaceutical composition is in the form of an immediate release capsule or an enteric coated capsule. In some embodiments, the pharmaceutical composition is in the form of a tablet. In some embodiments, the pharmaceutical composition is in the form of an immediate release tablet, an enteric coated tablet, or a sustained release tablet. In some embodiments, the pharmaceutical composition is in the form of a moisture barrier coated tablet. In some embodiments, the pharmaceutical composition comprises about 0.5 mg to about 1000 mg of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the pharmaceutical composition comprises about 30 mg to about 300 mg of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide.

Also provided is an article of manufacture comprising multiple unit doses of the oral solid dosage form pharmaceutical composition described herein in a high-density polyethylene (HDPE) bottle equipped with a high-density polyethylene (HDPE) cap. In some embodiments, high-density polyethylene (HDPE) bottle further comprises an aluminum foil induction seal and silica gel desiccant.

Also described is a method of treating prostate cancer in a mammal comprising administering to the mammal a pharmaceutical composition as described herein. In some embodiments, the prostate cancer is hormone sensitive prostate cancer or hormone refractory prostate cancer.

Also provided is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, for the manufacture of a medicament for the treatment or prevention of prostate cancer in a human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is crystalline.

Also described herein are processes for the preparation of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide. The disclosed processes provide for the preparation of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide in good yield and high purity.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

BRIEF DESCRIPTION OF THE FIGURES

FIG. 1 illustrates the XRPD of Form A.
FIG. 2 illustrates the XRPD of Form B.
FIG. 3 illustrates the XRPD of Form C.
FIG. 4 illustrates the XRPD of Form D.
FIG. 5 illustrates the XRPD of Form E.
FIG. 6 illustrates the XRPD of Form F.
FIG. 7 illustrates the XRPD of Form G.
FIG. 8 illustrates the XRPD of Form H.
FIG. 9 illustrates the XRPD of Form I.
FIG. 10 illustrates the XRPD of Form J.
FIG. 11 illustrates the TGA and DSC thermograms of Form B.
FIG. 12 illustrates the TGA and DSC thermograms of Form C.
FIG. 13 illustrates the TGA and DSC thermograms of Form D.
FIG. 14 illustrates the TGA and DSC thermograms of Form E.
FIG. 15 illustrates the TGA and DSC thermograms of Form F.
FIG. 16 illustrates the DSC thermogram of Form G.
FIG. 17 illustrates the TGA and DSC thermograms of Form H.
FIG. 18 illustrates the TGA and DSC thermograms of Form J.
FIG. 19 illustrates the DSC thermogram of Form A.

DETAILED DESCRIPTION OF THE INVENTION

The androgen receptor (AR) is a member of the nuclear receptor superfamily. Among this family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptorprotein interactions and receptor-DNA interactions.

AR is mainly expressed in androgen target tissues, such as the prostate, skeletal muscle, liver, and central nervous system (CNS), with higher expression levels observed in the prostate, adrenal gland, and epididymis. AR can be activated by the binding of endogenous androgens, including testosterone and 5α-dihydrotestosterone (5α-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (using GnRH agonists) continues to be the mainstay of prostate cancer treatment. However androgen depletion is usually effective for a limited duration and prostate cancer evolves to regain the ability to grow despite low levels of circulating androgens.

Treatment options for castration resistant prostate cancer (CRPC) are limited, with docetaxel and abiraterone acetate (a CYP17 inhibitor) being agents that have been shown to prolong survival. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g. GnRH agonists), alone or in combination with anti-androgens (e.g. bicalutamide), which antagonize the effect of any residual testosterone. The approach is effective as evidenced by a drop in PSA and regression of visible tumor (if present); however, this is followed by regrowth as a "castration resistant" prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (*Nat. Med,* 2004, 10, 33-39). AR targeting agents with activity in hormone sensitive and castration resistant prostate cancer have great promise in treating this lethal disease.

Anti-androgens are useful for the treatment of prostate cancer during its early stages. However, prostate cancer often advances to a hormone-refractory state in which the disease progresses in the presence of continued androgen ablation or anti-androgen therapy. Instances of anti-androgen withdrawal syndrome have also been reported after prolonged treatment with anti-androgens. Anti-androgen withdrawal syndrome is commonly observed clinically and is defined in terms of the tumor regression or symptomatic relief observed upon cessation of anti-androgen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered "castration resistant" via over expression of AR, it has been demonstrated that certain anti-androgen compounds, such as bicalutamide, have no antagonist activity, but instead have modest agonist activity (Science, 2009 May 8; 324(5928): 787-790). This agonist activity helps to explain a clinical observation, called the anti-androgen withdrawal syndrome, whereby about 30% of men who progress on AR antagonists experience a decrease in serum PSA when therapy is discontinued (*J Clin Oncol,* 1993. 11(8): p. 1566-72).

Given the central role of AR in prostate cancer development and progression, 4-[7-(6-cyano-5-trifluoromethylpyridin-3-yl)-8-oxo-6-thioxo-5,7-diazaspiro[3.4]oct-5-yl]-2-fluoro-N-methylbenzamide is useful in the treatment of prostate cancer.

AR-related diseases or conditions include, but are not limited to, benign prostate hyperplasia, hirsutism, acne, adenomas and neoplasias of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, Kennedy's disease muscle atrophy and weakness, skin atrophy, bone loss, anemia, arteriosclerosis, cardiovascular disease, loss of energy, loss of well-being, type 2 diabetes, and abdominal fat accumulation.

4-[7-(6-Cyano-5-trifluoromethylpyridin-3-yl)-8-oxo-6-thioxo-5,7-diazaspiro[3.4]oct-5-yl]-2-fluoro-N-methylbenzamide is an androgen receptor modulator that inhibits both AR nuclear translocation and AR binding to androgen response elements in DNA. Importantly, and in contrast to the first-generation anti-androgen bicalutamide, it exhibits no agonist activity in prostate cancer cells that over-express androgen receptors. It is well suited as either a mono- or a combination therapy across the entire spectrum of prostate cancer disease states.

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is used to treat prostate cancer in a mammal, wherein the mammal is chemotherapy-naïve.

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is used to treat prostate cancer in a mammal, wherein the mammal is being treated for prostate cancer with at least one anti-cancer agent. In one embodiment, the prostate cancer is hormone refractory prostate cancer. In one embodiment, the prostate cancer is bicalutamide-resistant prostate cancer.

4-[7-(6-Cyano-5-trifluoromethylpyridin-3-yl)-8-oxo-6-thioxo-5,7-diazaspiro[3.4]oct-5-yl]-2-fluoro-N-methylbenzamide, and Pharmaceutically Acceptable Salts Thereof "4-[7-(6-Cyano-5-trifluoromethylpyridin-3-yl)-8-oxo-6-thioxo-5,7-diazaspiro[3.4]oct-5-yl]-2-fluoro-N-methylbenzamide" refers to the compound with the following structure:

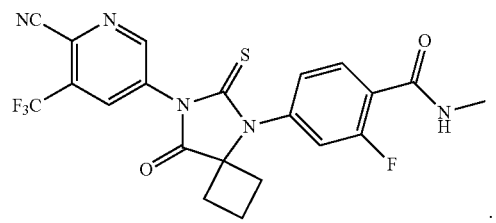 [SMILES: CNC(=O)c1ccc(N2C(=S)N(c3cnc(C#N)c(C(F)(F)F)c3)C(=O)C23CCC3)cc1F]

A wide variety of pharmaceutically acceptable salts of 4-[7-(6-cyano-5-trifluoromethylpyridin-3-yl)-8-oxo-6-thioxo-5,7-diazaspiro[3.4]oct-5-yl]-2-fluoro-N-methylbenzamide are possible and include acid addition salts, that are formed by reacting the free base of 4-[7-(6-cyano-5-trifluoromethylpyridin-3-yl)-8-oxo-6-thioxo-5,7-diazaspiro[3.4]oct-5-yl]-2-fluoro-N-methylbenzamide with an inorganic acid or an organic acid. Such salt forms of 4-[7-(6-cyano-5-trifluoromethylpyridin-3-yl)-8-oxo-6-thioxo-5,7-diazaspiro[3.4]oct-5-yl]-2-fluoro-N-methylbenzamide include, but are not limited to: hydrochloric acid salt, hydrobromic acid salt, sulfuric acid salt, phosphoric acid salt, metaphosphoric acid salt, acetic acid salt, propionic acid salt, hexanoic acid salt, cyclopentanepropionic acid salt, glycolic acid salt, pyruvic acid salt, lactic acid salt, malonic acid salt, succinic acid salt, malic acid salt, maleic acid salt, fumaric acid salt, trifluoroacetic acid salt, tartaric acid salt, citric acid salt, benzoic acid salt, 3-(4-hydroxybenzoyl)benzoic acid salt, cinnamic acid salt, mandelic acid salt, methanesulfonic acid salt, ethanesulfonic acid salt, 1,2-ethanedisulfonic acid salt, 2-hydroxyethanesulfonic acid salt, benzenesulfonic acid salt, toluenesulfonic acid salt, 2-naphthalenesulfonic acid salt, 4-methylbicyclo-[2.2.2]oct-2-ene-1-carboxylic acid salt, glucoheptonic acid salt, 3-phenylpropionic acid salt, trimethylacetic acid salt, tertiary butylacetic acid salt, lauryl sulfuric acid salt, gluconic acid salt, glutamic acid salt, hydroxynaphthoic acid salt, salicylic acid salt, stearic acid salt, muconic acid salt, butyric acid salt, phenylacetic acid salt, phenylbutyric acid salt, valproic acid salt, and the like.

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is used in any of the pharmaceutical compositions or methods described herein.

In some embodiments, a pharmaceutically acceptable salt of 4-[7-(6-cyano-5-trifluoromethylpyridin-3-yl)-8-oxo-6-thioxo-5,7-diazaspiro[3.4]oct-5-yl]-2-fluoro-N-methylbenzamide is used in any of the pharmaceutical compositions or methods described herein.

The term "pharmaceutically acceptable salt" in reference to 4-[7-(6-cyano-5-trifluoromethylpyridin-3-yl)-8-oxo-6-thioxo-5,7-diazaspiro[3.4]oct-5-yl]-2-fluoro-N-methylbenzamide refers to a salt of 4-[7-(6-cyano-5-trifluoromethyl-pyridin-3-yl)-8-oxo-6-thioxo-5,7-diazaspiro[3.4]oct-5-yl]-2-fluoro-N-methylbenzamide, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methyl tert-butyl ether, isopropanol, acetonitrile, heptane, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is an alcohol. In one embodiment, solvates of 4-[7-(6-cyano-5-trifluoromethylpyridin-3-yl)-8-oxo-6-thioxo-5,7-diazaspiro[3.4]oct-5-yl]-2-fluoro-N-methylbenzamide, or salts thereof, are conveniently prepared or formed during the processes described herein. In other embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide, or salts thereof, exist in unsolvated form.

In yet other embodiments, 4-[7-(6-cyano-5-trifluorometh-ylpyridin-3-yl)-8-oxo-6-thioxo-5,7-diazaspiro[3.4]oct-5-yl]-2-fluoro-N-methylbenzamide or a pharmaceutically acceptable salt thereof is prepared in various forms, including but not limited to, amorphous phase, milled forms, and nano-particulate forms.

Amorphous 4-[7-(6-Cyano-5-trifluoromethylpyridin-3-yl)-8-oxo-6-thioxo-5,7-diazaspiro[3.4]oct-5-yl]-2-fluoro-N-methylbenzamide In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is amorphous. In some embodiments, Amorphous Phase of 4-[7-(6-cyano-5-trifluoromethylpyridin-3-yl)-8-oxo-6-thioxo-5,7-diazaspiro[3.4]oct-5-yl]-2-fluoro-N-methylbenzamide has an XRPD pattern showing a lack of crystallinity.

Form A

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form A. Form A of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as exhibiting at least one of:

(a) an X-Ray powder diffraction (XRPD) pattern substantially the same as shown in FIG. 1;
(b) an X-ray powder diffraction (XRPD) pattern with characteristic peaks at 4.8±0.1° 2-Theta, 7.1±0.1° 2-Theta, 14.2±0.1° 2-Theta, 16.3±0.1° 2-Theta, 20.1±0.1° 2-Theta;
(c) unit cell parameters substantially equal to the following at −173° C.:

| Crystal system | | Orthorhombic | | |
|---|---|---|---|---|
| Space group | P2(1)2(1)2 | | | |
| | a | 16.3429(3) Å | α | 90° |
| | b | 37.7298(7) Å | β | 90° |
| | c | 7.23410(10) Å | γ | 90° |
| V | | 4460.65(13) Å$^3$ | | |
| Z | | 8 | | |
| Dc | | 1.446 g · cm$^{-1}$ | | |

(d) substantially the same X-ray powder diffraction (XRPD) pattern post storage at 40° C. and 75% RH for at least a week;
(e) a DSC thermogram with an endotherm having an onset temperature at about 108-120° C. and a peak at about 133-135° C.;
(f) a DSC thermogram substantially similar to the one set forth in FIG. 19;
(g) an observed aqueous solubility of about 0.01 mg/mL; or
(h) combinations thereof.

In some embodiments, Form A is characterized as exhibiting at least two, at least three, at least four, at least five, at least six or all seven of the properties selected from (a) to (g). In some embodiments, Form A is characterized as having properties (a), (b), (c), (d), (e), (f) and (g). In some embodiments, Form A is characterized as having property (a), (b), (c), (d), (g) or combinations thereof. In some embodiments, Form A is characterized as having at least two, at least three, at least four or all five of the properties selected from (a), (b), (c), (d), and (g). In some embodiments, Form A is characterized as having properties (a), (b), (c), (d), and (g).

In some embodiments, Form A is characterized as having an X-Ray powder diffraction (XRPD) pattern substantially the same as shown in FIG. 1. In some embodiments, Form A is characterized as having an X-ray powder diffraction (XRPD) pattern with characteristic peaks at 4.8±0.1° 2-Theta, 7.1±0.1° 2-Theta, 14.2±0.1° 2-Theta, 16.3±0.1° 2-Theta, 20.1±0.1° 2-Theta. In some embodiments, Form A is characterized as having substantially the same X-ray powder diffraction (XRPD) pattern post storage at 40° C. and 75% RH for at least a week.

In some embodiments, Form A is characterized as having unit cell parameters substantially equal to the following at −173° C.:

| Crystal system | | | Orthorhombic | | |
|---|---|---|---|---|---|
| Space group | P2(1)2(1)2 | a | 16.3429(3) Å | α | 90° |
| | | b | 37.7298(7) Å | β | 90° |
| | | c | 7.23410(10) Å | γ | 90° |
| V | | | 4460.65(13) Å³ | | |
| Z | | | 8 | | |
| Dc | | | 1.446 g · cm⁻¹ | | |

In some embodiments, Form A is characterized as having a DSC thermogram with an endotherm having an onset temperature at about 108-120° C. and a peak at about 133-135° C.;

In some embodiments, Form A is characterized as having a DSC thermogram substantially similar to the one set forth in FIG. 19.

In some embodiments, Form A is characterized as having an observed aqueous solubility of about 0.01 mg/mL In some embodiments, Form A is obtained from ethanol, tetrahydrofuran (THF), dichloromethane, acetone, methanol, nitromethane, water, THF-water mixture, or dioxane-water mixture. In some embodiments, Form A is obtained from ethanol. In some embodiments, Form A is solvated. In some embodiments, Form A is an ethanol solvate. In some embodiments, Form A is unsolvated. In some embodiments, Form A is a hydrate. In some embodiments, Form A is a solvated hydrate.

Form B

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form B. Form B is unsolvated. Form B of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 2;
(b) an X-ray powder diffraction (XRPD) pattern with characteristic peaks at 12.1±0.1° 2-Theta, 16.0±0.1° 2-Theta, 16.7±0.1° 2-Theta, 20.1±0.1° 2-Theta, 20.3±0.1° 2-Theta;
(c) unit cell parameters substantially equal to the following at −173° C.:

| Crystal system | | | Monoclinic | | |
|---|---|---|---|---|---|
| Space group | P2₁/c | a | 17.7796(4) Å | α | 90° |
| | | b | 12.9832(3) Å | β | 100.897(2)° |
| | | c | 18.4740(4) Å | γ | 90° |
| V | | | 4187.57(16) Å³ | | |
| Z | | | 8 | | |
| Dc | | | 1.515 g · cm⁻¹ | | |

(d) a DSC thermogram substantially similar to the one set forth in FIG. 11;
(e) a thermo-gravimetric analysis (TGA) thermogram substantially similar to the one set forth in FIG. 11;
(f) a DSC thermogram with an endotherm having an onset temperature at about 194° C.;
(g) substantially the same X-ray powder diffraction (XRPD) pattern post storage at 40° C. and 75% RH for at least a week;
(h) substantially the same X-ray powder diffraction (XRPD) pattern post storage at 25° C. and 92% RH for 12 days;
(i) an observed aqueous solubility of about 0.004 mg/mL; or
(j) combinations thereof.

In some embodiments, Form B is characterized as having at least two, at least three, at least four, at least five, at least six, at least seven, at least eight or all nine of the properties selected from (a) to (i).

In some embodiments, Form B is characterized as having an X-Ray powder diffraction (XRPD) pattern substantially the same as shown in FIG. 2. In some embodiments, Form B is characterized as having an X-ray powder diffraction (XRPD) pattern with characteristic peaks at 12.1±0.1° 2-Theta, 16.0±0.1° 2-Theta, 16.7±0.1° 2-Theta, 20.1±0.1° 2-Theta, 20.3±0.1° 2-Theta. In some embodiments, Form B is characterized as having substantially the same X-ray powder diffraction (XRPD) pattern post storage at 40° C. and 75% RH for at least a week. In some embodiments, Form B is characterized as having substantially the same X-ray powder diffraction (XRPD) pattern post storage at 25° C. and 92% RH for 12 days.

In some embodiments, Form B is characterized as having unit cell parameters substantially equal to the following at −173° C.:

| Crystal system | | | Monoclinic | | |
|---|---|---|---|---|---|
| Space group | P2₁/c | a | 17.7796(4) Å | α | 90° |
| | | b | 12.9832(3) Å | β | 100.897(2)° |
| | | c | 18.4740(4) Å | γ | 90° |
| V | | | 4187.57(16) Å³ | | |
| Z | | | 8 | | |
| Dc | | | 1.515 g · cm⁻¹ | | |

In some embodiments, Form B is characterized as having a DSC thermogram substantially similar to the one set forth in FIG. 11. In some embodiments, Form B is characterized as having a thermo-gravimetric analysis (TGA) thermogram substantially similar to the one set forth in FIG. 11. In some embodiments, Form B is characterized as having a DSC thermogram with an endotherm having an onset temperature at about 194° C.

In some embodiments, Form B is characterized as having an observed aqueous solubility of about 0.004 mg/mL.

In some embodiments, Form B is obtained from water, ethyl acetate, tert-butyl methyl ether (TBME), toluene, isopropylacetate, or methyl ethyl ketone (MEK).

Form C

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form C. Form C of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 3;
(b) an X-ray powder diffraction (XRPD) pattern with characteristic peaks at 4.3±0.1° 2-Theta, 6.9±0.1° 2-Theta, 9.1±0.1° 2-Theta, 10.6±0.1° 2-Theta, 13.8±0.1° 2-Theta, 26.4±0.1° 2-Theta;
(c) a DSC thermogram substantially similar to the one set forth in FIG. 12;
(d) a thermo-gravimetric analysis (TGA) thermogram substantially similar to the one set forth in FIG. 12;
(e) a DSC thermogram with a first endotherm having an onset temperature at about 118° C. and second endotherm having an onset temperature at about 193° C.;

(f) substantially the same X-ray powder diffraction (XRPD) pattern post storage at 40° C. and 75% RH for at least a week;
or
(g) combinations thereof.

In some embodiments, Form C is characterized as having at least two, at least three, at least four, at least five, or all six of the properties selected from (a) to (f).

In some embodiments, Form C is characterized as having an X-Ray powder diffraction (XRPD) pattern substantially the same as shown in FIG. 3. In some embodiments, Form C is characterized as having an X-ray powder diffraction (XRPD) pattern with characteristic peaks at 4.3±0.1° 2-Theta, 6.9±0.1° 2-Theta, 9.1±0.1° 2-Theta, 10.6±0.1° 2-Theta, 13.8±0.1° 2-Theta, 26.4±0.1° 2-Theta. In some embodiments, Form C is characterized as having substantially the same X-ray powder diffraction (XRPD) pattern post storage at 40° C. and 75% RH for at least a week.

In some embodiments, Form C is characterized as having a DSC thermogram substantially similar to the one set forth in FIG. 12. In some embodiments, Form C is characterized as having a thermo-gravimetric analysis (TGA) thermogram substantially similar to the one set forth in FIG. 12. In some embodiments, Form C is characterized as having a DSC thermogram with a first endotherm having an onset temperature at about 118° C. and second endotherm having an onset temperature at about 193° C.

In some embodiments, Form C is obtained from isopropanol (IPA), anisole, or IPA-water mixture. In some embodiments, Form C is solvated. In some embodiments, Form C is an isopropanol solvate.

Form D

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form D. Form D of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:
(a) an X-Ray powder diffraction (XRPD) pattern substantially the same as shown in FIG. 4;
(b) an X-ray powder diffraction (XRPD) pattern with characteristic peaks at 6.3±0.1° 2-Theta, 13.9±0.1° 2-Theta, 16.4±0.1° 2-Theta, 17.0±0.1° 2-Theta, 23.7±0.1° 2-Theta, 24.8±0.1° 2-Theta;
(c) a DSC thermogram substantially similar to the one set forth in FIG. 13;
(d) a thermo-gravimetric analysis (TGA) thermogram substantially similar to the one set forth in FIG. 13;
(e) a DSC thermogram with a first endotherm having an onset temperature at about 122° C. and second endotherm having an onset temperature at about 192° C.;
(f) substantially the same X-ray powder diffraction (XRPD) pattern post storage at 40° C. and 75% RH for at least a week;
or
(g) combinations thereof.

In some embodiments, Form D is characterized as having at least two, at least three, at least four, at least five, or all six of the properties selected from (a) to (f).

In some embodiments, Form D is characterized as having an X-Ray powder diffraction (XRPD) pattern substantially the same as shown in FIG. 4. In some embodiments, Form D is characterized as having an X-ray powder diffraction (XRPD) pattern with characteristic peaks at 6.3±0.1° 2-Theta, 13.9±0.1° 2-Theta, 16.4±0.1° 2-Theta, 17.0±0.1° 2-Theta, 23.7±0.1° 2-Theta, 24.8±0.1° 2-Theta. In some embodiments, Form D is characterized as having substantially the same X-ray powder diffraction (XRPD) pattern post storage at 40° C. and 75% RH for at least a week.

In some embodiments, Form D is characterized as having a DSC thermogram substantially similar to the one set forth in FIG. 13. In some embodiments, Form D is characterized as having a thermo-gravimetric analysis (TGA) thermogram substantially similar to the one set forth in FIG. 13. In some embodiments, Form D is characterized as having a DSC thermogram with an endotherm having an onset temperature at about 122° C. In some embodiments, Form D is characterized as having a DSC thermogram with a first endotherm having an onset temperature at about 122° C. and second endotherm having an onset temperature at about 192° C.

In some embodiments, Form D is obtained from tert-butyl methyl ether (TBME). In some embodiments, Form D is solvated. In some embodiments, Form D is a tert-butyl methyl ether (TBME) solvate.

Form E

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form E. Form E of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:
(a) an X-Ray powder diffraction (XRPD) pattern substantially the same as shown in FIG. 5;
(b) an X-ray powder diffraction (XRPD) pattern with characteristic peaks at 7.2±0.1° 2-Theta, 11.8±0.1° 2-Theta, 16.1±0.1° 2-Theta, 20.5±0.1° 2-Theta, 23.0±0.1° 2-Theta, 25.2±0.1° 2-Theta;
(c) unit cell parameters substantially equal to the following at −173° C.:

| Crystal system | | Orthorhombic | | |
|---|---|---|---|---|
| Space group | $P_{na}2_1$ | a   8.43080(10) Å | α | 90° |
| | | b   17.1685(3) Å | β | 90° |
| | | c   17.4276(3) Å | γ | 90° |
| V | | 2522.54(7) Å$^3$ | | |
| Z | | 4 | | |
| Dc | | 1.463 g · cm$^{-1}$ | | |

(d) a DSC thermogram substantially similar to the one set forth in FIG. 14;
(e) a thermo-gravimetric analysis (TGA) thermogram substantially similar to the one set forth in FIG. 14;
(f) a DSC thermogram with an endotherm having an onset temperature at about 116° C.;
or
(g) combinations thereof.

In some embodiments, Form E is characterized as having at least two, at least three, at least four, at least five, or all six of the properties selected from (a) to (f).

In some embodiments, Form E is characterized as having an X-Ray powder diffraction (XRPD) pattern substantially the same as shown in FIG. 5. In some embodiments, Form E is characterized as having an X-ray powder diffraction (XRPD) pattern with characteristic peaks at 7.2±0.1° 2-Theta, 11.8±0.1° 2-Theta, 16.1±0.1° 2-Theta, 20.5±0.1° 2-Theta, 23.0±0.1° 2-Theta, 25.2±0.1° 2-Theta.

In some embodiments, Form E is characterized as having unit cell parameters substantially equal to the following at −173° C.:

| Crystal system | Orthorhombic | | | | |
|---|---|---|---|---|---|
| Space group | $P_{na}2_1$ | a | 8.43080(10) Å | α | 90° |
| | | b | 17.1685(3) Å | β | 90° |
| | | c | 17.4276(3) Å | γ | 90° |
| V | | | 2522.54(7) Å³ | | |
| Z | | | 4 | | |
| Dc | | | 1.463 g·cm⁻¹ | | |

In some embodiments, Form E is characterized as having a DSC thermogram substantially similar to the one set forth in FIG. 14. In some embodiments, Form E is characterized as having a thermo-gravimetric analysis (TGA) thermogram substantially similar to the one set forth in FIG. 14. In some embodiments, Form E is characterized as having a DSC thermogram with an endotherm having an onset temperature at about 116° C.

In some embodiments, Form E is obtained from dimethylsulfoxide. In some embodiments, Form E is solvated. In some embodiments, Form E is a dimethylsulfoxide solvate.

Form F

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form F. Form F of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 6;
(b) an X-ray powder diffraction (XRPD) pattern with characteristic peaks at 4.6±0.1° 2-Theta, 6.1±0.1° 2-Theta, 14.3±0.1° 2-Theta, 21.6±0.1° 2-Theta, 22.4±0.1° 2-Theta, 23.3±0.1° 2-Theta, 25.5±0.1° 2-Theta;
(c) a DSC thermogram substantially similar to the one set forth in FIG. 15;
(d) a thermo-gravimetric analysis (TGA) thermogram substantially similar to the one set forth in FIG. 15;
(e) a DSC thermogram with an endotherm having an onset temperature at about 113° C.;
or
(f) combinations thereof.

In some embodiments, Form F is characterized as having at least two, at least three, at least four, or all five of the properties selected from (a) to (e).

In some embodiments, Form F is characterized as having an X-Ray powder diffraction (XRPD) pattern substantially the same as shown in FIG. 6. In some embodiments, Form F is characterized as having an X-ray powder diffraction (XRPD) pattern with characteristic peaks at 4.6±0.1° 2-Theta, 6.1±0.1° 2-Theta, 14.3±0.1° 2-Theta, 21.6±0.1° 2-Theta, 22.4±0.1° 2-Theta, 23.3±0.1° 2-Theta, 25.5±0.1° 2-Theta.

In some embodiments, Form F is characterized as having a DSC thermogram substantially similar to the one set forth in FIG. 15. In some embodiments, Form F is characterized as having a thermo-gravimetric analysis (TGA) thermogram substantially similar to the one set forth in FIG. 15. In some embodiments, Form F is characterized as having a DSC thermogram with an endotherm having an onset temperature at about 113° C.

In some embodiments, Form F is obtained from an acetone/water mixture.

Form G

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form G. Form G of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 7;
(b) an X-ray powder diffraction (XRPD) pattern with characteristic peaks at 7.0±0.1° 2-Theta, 10.3±0.1° 2-Theta, 14.1±0.1° 2-Theta, 15.2±0.1° 2-Theta, 23.6±0.1° 2-Theta;
(c) unit cell parameters substantially equal to the following at −173° C.:

| Crystal system | | | Monoclinic | | |
|---|---|---|---|---|---|
| Space group | Cc | a | 18.613(2) Å | α | 90° |
| | | b | 16.9728(14) Å | β | 91.328(8)° |
| | | c | 7.8214(7) Å, | γ | 90° |
| V | | | 2470.2(4) Å³ | | |
| Z | | | 4 | | |
| Dc | | | 1.488 g·cm⁻¹ | | |

(d) a DSC thermogram substantially similar to the one set forth in FIG. 16;
(e) a DSC thermogram with a first endotherm having an onset temperature at about 101° C. and second endotherm having an onset temperature at about 190° C.;
(f) substantially the same X-ray powder diffraction (XRPD) pattern post storage at 40° C. and 75% RH for at least a week;
or
(g) combinations thereof.

In some embodiments, Form G is characterized as having at least two, at least three, at least four, at least five, or all six of the properties selected from (a) to (f).

In some embodiments, Form G is characterized as having an X-Ray powder diffraction (XRPD) pattern substantially the same as shown in FIG. 7. In some embodiments, Form G is characterized as having an X-ray powder diffraction (XRPD) pattern with characteristic peaks at 7.0±0.1° 2-Theta, 10.3±0.1° 2-Theta, 14.1±0.1° 2-Theta, 15.2±0.1° 2-Theta, 23.6±0.1° 2-Theta.

In some embodiments, Form G is characterized as having unit cell parameters substantially equal to the following at −173° C.:

| Crystal system | | | Monoclinic | | |
|---|---|---|---|---|---|
| Space group | Cc | a | 18.613(2) Å | α | 90° |
| | | b | 16.9728(14) Å | β | 91.328(8)° |
| | | c | 7.8214(7) Å, | γ | 90° |
| V | | | 2470.2(4) Å³ | | |
| Z | | | 4 | | |
| Dc | | | 1.488 g·cm⁻¹ | | |

In some embodiments, Form G is characterized as having a DSC thermogram substantially similar to the one set forth in FIG. 16. In some embodiments, Form G is characterized as having a DSC thermogram with an endotherm having an onset temperature at about 101° C. In some embodiments, Form G is characterized as having a DSC thermogram with a first endotherm having an onset temperature at about 101° C. and second endotherm having an onset temperature at about 190° C.

In some embodiments, Form G is characterized as having substantially the same X-ray powder diffraction (XRPD) pattern post storage at 40° C. and 75% RH for at least a week.

In some embodiments, Form G is obtained from 2-methoxyethanol. In some embodiments, Form G is solvated. In some embodiments, Form G is a 2-methoxyethanol solvate.

Form H

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form H. Form H is unsolvated. Form H of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 8;
(b) an X-ray powder diffraction (XRPD) pattern with characteristic peaks at 8.0±0.1° 2-Theta, 14.7±0.1° 2-Theta, 15.9±0.1° 2-Theta, 18.2±0.1° 2-Theta, 25.7±0.1° 2-Theta, 26.7±0.1° 2-Theta;
(c) a DSC thermogram substantially similar to the one set forth in FIG. 17;
(d) a thermo-gravimetric analysis (TGA) thermogram substantially similar to the one set forth in FIG. 17;
(e) a DSC thermogram with a first endotherm having an onset temperature at about 173° C. and second endotherm having an onset temperature at about 193° C.;
(f) substantially the same X-ray powder diffraction (XRPD) pattern post storage at 40° C. and 75% RH for at least a week;
or
(g) combinations thereof.

In some embodiments, Form H is characterized as having at least two, at least three, at least four, at least five, or all six of the properties selected from (a) to (f).

In some embodiments, Form H is characterized as having an X-Ray powder diffraction (XRPD) pattern substantially the same as shown in FIG. 8. In some embodiments, Form H is characterized as having an X-ray powder diffraction (XRPD) pattern with characteristic peaks at 8.0±0.1° 2-Theta, 14.7±0.1° 2-Theta, 15.9±0.1° 2-Theta, 18.2±0.1° 2-Theta, 25.7±0.1° 2-Theta, 26.7±0.1° 2-Theta. In some embodiments, Form H is characterized as having substantially the same X-ray powder diffraction (XRPD) pattern post storage at 40° C. and 75% RH for at least a week.

In some embodiments, Form H is characterized as having a DSC thermogram substantially similar to the one set forth in FIG. 17. In some embodiments, Form H is characterized as having a thermo-gravimetric analysis (TGA) thermogram substantially similar to the one set forth in FIG. 17. In some embodiments, Form H is characterized as having a DSC thermogram with a first endotherm having an onset temperature at about 173° C. and second endotherm having an onset temperature at about 193° C.

In some embodiments, Form H is obtained from ethyl acetate.

Form I

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form I. Form I of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 9;
(b) an X-ray powder diffraction (XRPD) pattern with characteristic peaks 7.7±0.1° 2-Theta, 10.4±0.1° 2-Theta, 11.6±0.1° 2-Theta, 17.0±0.1° 2-Theta, 20.0±0.1° 2-Theta, 20.6±0.1° 2-Theta;
or
(c) combinations thereof.

In some embodiments, Form I is characterized as having at least property (a) and property (b).

In some embodiments, Form I is characterized as having an X-Ray powder diffraction (XRPD) pattern substantially the same as shown in FIG. 9. In some embodiments, Form I is characterized as having an X-ray powder diffraction (XRPD) pattern with characteristic peaks 7.7±0.1° 2-Theta, 10.4±0.1° 2-Theta, 11.6±0.1° 2-Theta, 17.0±0.1° 2-Theta, 20.0±0.1° 2-Theta, 20.6±0.1° 2-Theta.

In some embodiments, Form I is obtained from dimethylsulfoxide.

Form J

In some embodiments, 4-[7-(6-cyano-5-trifluoromethyl-pyridin-3-yl)-8-oxo-6-thioxo-5,7-diazaspiro[3.4]oct-5-yl]-2-fluoro-N-methylbenzamide is crystalline. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is Form J. Form J of 4-[7-(6-cyano-5-trifluoromethylpyridin-3-yl)-8-oxo-6-thioxo-5,7-diazaspiro[3.4]oct-5-yl]-2-fluoro-N-methylbenzamide is characterized as having:

(a) an X-Ray powder diffraction (XRPD) pattern substantially the same as shown in FIG. 10;
(b) an X-ray powder diffraction (XRPD) pattern with characteristic peaks at 8.6±0.1° 2-Theta, 19.3±0.1° 2-Theta, 20.8±0.1° 2-Theta, 24.3±0.1° 2-Theta, 27.6±0.1° 2-Theta;
(c) a DSC thermogram substantially similar to the one set forth in FIG. 18;
(d) a thermo-gravimetric analysis (TGA) thermogram substantially similar to the one set forth in FIG. 18;
(e) a DSC thermogram with a first endotherm having an onset temperature at about 104° C. and second endotherm having an onset temperature at about 193° C.;
or
(f) combinations thereof.

In some embodiments, Form J is characterized as having at least two, at least three, at least four, or all least five of the properties selected from (a) to (e).

In some embodiments, Form J is characterized as having an X-Ray powder diffraction (XRPD) pattern substantially the same as shown in FIG. 10. In some embodiments, Form J is characterized as having an X-ray powder diffraction (XRPD) pattern with characteristic peaks at 8.6±0.1° 2-Theta, 19.3±0.1° 2-Theta, 20.8±0.1° 2-Theta, 24.3±0.1° 2-Theta, 27.6±0.1° 2-Theta.

In some embodiments, Form J is characterized as having a DSC thermogram substantially similar to the one set forth in FIG. 18. In some embodiments, Form J is characterized as having a thermo-gravimetric analysis (TGA) thermogram substantially similar to the one set forth in FIG. 18. In some embodiments, Form J is characterized as having a DSC thermogram with an endotherm having an onset temperature at about 104° C. In some embodiments, Form J is characterized as having a DSC thermogram with a first endotherm having an onset temperature at about 104° C. and second endotherm having an onset temperature at about 193° C.

In some embodiments, Form J is obtained from a mixture of acetone and water. In some embodiments, Form J is solvated. In some embodiments, Form J is an acetone solvate.

Preparation of Crystalline Forms

In some embodiments, crystalline forms of 4-[7-(6-cyano-5-trifluoromethylpyridin-3-yl)-8-oxo-6-thioxo-5,7-diazaspiro[3.4]oct-5-yl]-2-fluoro-N-methylbenzamide are prepared as outlined in the Examples. It is noted that solvents, temperatures and other reaction conditions presented herein may vary.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

In some embodiments, compositions comprising 4-[7-(6-cyano-5-trifluoromethylpyridin-3-yl)-8-oxo-6-thioxo-5,7-diazaspiro[3.4]oct-5-yl]-2-fluoro-N-methylbenzamide include a residual amount of an organic solvent(s). In some embodiments, compositions comprising 4-[7-(6-cyano-5-trifluoromethylpyridin-3-yl)-8-oxo-6-thioxo-5,7-diazaspiro[3.4]oct-5-yl]-2-fluoro-N-methylbenzamide include a detectable amount of an organic solvent(s). In some embodiments, compositions comprising 4-[7-(6-cyano-5-trifluoromethylpyridin-3-yl)-8-oxo-6-thioxo-5,7-diazaspiro[3.4]oct-5-yl]-2-fluoro-N-methylbenzamide include a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is ethanol.

The methods and compositions described herein include the use of crystalline forms of 4-[7-(6-cyano-5-trifluoromethylpyridin-3-yl)-8-oxo-6-thioxo-5,7-diazaspiro[3.4]oct-5-yl]-2-fluoro-N-methylbenzamide. In addition, the crystalline forms of 4-[7-(6-cyano-5-trifluoromethylpyridin-3-yl)-8-oxo-6-thioxo-5,7-diazaspiro[3.4]oct-5-yl]-2-fluoro-N-methylbenzamide described herein can exist in unsolvated as well as solvated forms with pharmaceutically acceptable solvents such as water, ethanol, and the like.

Definitions

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, an API is crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the API has a purity of greater than 90%, greater than 95%, greater than 96%, greater than 97%, greater than 98%, greater than 98%, or greater than 99%.

The term "pharmaceutical composition" refers to a mixture of 4-[7-(6-cyano-5-trifluoromethylpyridin-3-yl)-8-oxo-6-thioxo-5,7-diazaspiro[3.4]oct-5-yl]-2-fluoro-N-methylbenzamide, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc) (ICH guidances, *Q2A Text on*

*Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, AR trafficking modulator, AR DNA-binding inhibitor. In some embodiments, a modulator is an antagonist. In some embodiments, a modulator is an inverse agonist, antagonist, degrader, AR trafficking modulator and/or a DNA binding inhibitor.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor.

The term "AR trafficking modulator" as used herein, refers to a small-molecule agent that binds to a nuclear hormone receptor and subsequently alters the normal subcellular location of the receptor thereby interfering with its function and signaling.

The term "DNA-binding inhibitor" as used herein, refers to a small-molecule agent that binds to a nuclear hormone receptor and subsequently prevents DNA binding of the receptor thereby interfering with its function and signaling.

"Selective" with respect to androgen receptors means that the compound preferentially binds to androgen receptors versus other nuclear receptors. In some embodiments, a selective androgen receptor modulator preferentially binds to androgen receptors and displays little, if any, affinity to other nuclear receptors.

The term "cancer" as used herein refers to an abnormal growth of cells which tend to proliferate in an uncontrolled way and, in some cases, to metastasize (spread).

The term "subject" or "patient" encompasses mammals. In one aspect, the mammal is a human. In another aspect, the mammal is a non-human primate such as chimpanzee, and other apes and monkey species. In one aspect, the mammal is a farm animal such as cattle, horse, sheep, goat, or swine. In one aspect, the mammal is a domestic animal such as rabbit, dog, or cat. In one aspect, the mammal is a laboratory animal, including rodents, such as rats, mice and guinea pigs, and the like.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is formulated for oral administration to a mammal. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is formulated into an oral dosage form. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is formulated into a solid oral dosage form. In some embodiments, crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide is formulated into a tablet, powder, pill, capsule, and the like, for oral ingestion by a mammal.

Contemplated pharmaceutical compositions provide a therapeutically effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide enabling, for example, once-a-day, twice-a-day, three times a day, etc. administration. In one aspect, pharmaceutical compositions provide an effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide enabling once-a-day dosing.

Dose Amounts

In certain embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide in the pharmaceutical compositions is about 0.3 mg to about 1.5 g per dose, 0.3 mg to about 1 g per dose, about 1 mg to about 1 g per dose.

In one embodiment, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide in the pharmaceutical compositions is about 1 mg per dose, about 5 mg per dose, about 10 mg per dose, about 15 mg per dose, about 30 mg per dose, about 45 mg per dose, about 60 mg per dose, about 100 mg per dose, about 150 mg per dose, about 200 mg per dose, about 300 mg per dose, about 400 mg per dose, about 500 mg per dose, about 600 mg per dose, or about 1000 mg per dose. In some embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide in the pharmaceutical compositions is about 30 mg per dose. In some other embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide in the pharmaceutical compositions is about 60 mg per dose.

In general, doses employed for adult human treatment are typically in the range of 0.01 mg-5000 mg per day. In one aspect, doses employed for adult human treatment are from about 1 mg to about 1000 mg per day. In some embodiments, doses employed for adult human treatment are about 240 mg per day. In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for 4-[7-(6-cyano-5-trifluoromethylpyridin-3-yl)-8-oxo-6-thioxo-5,7-diazaspiro[3.4]oct-5-yl]-2-fluoro-N-methylbenzamide is from about 0.01 to about 20 mg/kg per body weight. In other embodiments, the daily dosage or the amount of active in the dosage form are lower or higher than the ranges indicated herein.

Methods of Dosing and Treatment Regimens

In one embodiment, the pharmaceutical compositions including 4-[7-(6-cyano-5-trifluoromethylpyridin-3-yl)-8-oxo-6-thioxo-5,7-diazaspiro[3.4]oct-5-yl]-2-fluoro-N-methylbenzamide described herein are administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, compositions containing 4-[7-(6-cyano-5-trifluoromethylpyridin-3-yl)-8-oxo-6-thioxo-5,7-diazaspiro[3.4]oct-5-yl]-2-fluoro-N-methylbenzamide described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration.

In some embodiments, administration of the compound, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

Combination Treatments

In certain instances, it is appropriate to administer 4-[7-(6-cyano-5-trifluoromethylpyridin-3-yl)-8-oxo-6-thioxo-5,7-diazaspiro[3.4]oct-5-yl]-2-fluoro-N-methylbenzamide in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, the compounds are administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

For combination therapies described herein, dosages of the co-administered compounds vary depending on the type of co-drug employed, on the specific drug employed, on the disease or condition being treated and so forth.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Kits/Articles of Manufacture

For use in the therapeutic methods of use described herein, kits/articles of manufacture are also described herein. Such kits include a carrier, package, or container that is optionally compartmentalized to receive one or more doses of a pharmaceutical composition of 4-[7-(6-cyano-5-trifluoromethylpyridin-3-yl)-8-oxo-6-thioxo-5,7-diazaspiro[3.4]oct-5-yl]-2-fluoro-N-methylbenzamide for use in a method described herein. The kits provided herein contain packaging materials. Packaging materials for use in packaging pharmaceutical products include, but are not limited to those described in e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by treatment with an AR antagonist.

For example, the container(s) include 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

The following ingredients, formulations, processes and procedures for practicing the methods disclosed herein correspond to that described above. The procedures below describe with particularity illustrative, non-limiting embodiment of formulations that include a 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt and/or solvate thereof, and pharmacokinetic profiles and pharmacodynamic effects thereof. By way of example only, 4-[7-(6-cyano-5-trifluoromethylpyridin-3-yl)-8-oxo-6-thioxo-5,7-diazaspiro[3.4]oct-5-yl]-2-fluoro-N-methylbenzamide is optionally prepared as outlined in U.S. patent application Ser. No. 12/294,881, U.S. patent application Ser. No. 12/450,423 or as outlined herein.

Example 1: Preparation of Crystalline Forms of 4-[7-(6-cyano-5-trifluoromethylpyridin-3-yl)-8-oxo-6-thioxo-5,7-diazaspiro[3.4]oct-5-yl]-2-fluoro-N-methylbenzamide Form A 2 volumes of ethanol were added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (180 mg). After 6 days the material was filtered. The sample was placed in an oven at 35° C. and ca. 40 mbar pressure for an hour. The isolated material was shown to be an ethanol solvate by TGA, DSC, GVS and $^1$H NMR analysis. Under forcing conditions (60° C. at <20 mm Hg for 8 days), Form A lost ethanol, the XRPD pattern of the material stayed the same.

Alternatively, THF (1 volume), DCM (1 volume), acetone (1 volume), ethanol (1 volume), methanol (1 volume), nitromethane (1 volume), water (1 volume+sonication), THF-water mixture (1 volume), or dioxane-water mixture (1 volume) was added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The samples were left in screw capped vials at ambient conditions for 3 days. Lids on the samples which showed no precipitation were loosened to allow for slow evaporation of the solvent. After a day, these samples were placed in a maturation chamber, the temperature of which was switched between room temperature and 50° C. every 4 hours. Solid material was isolated. The single crystal XRD studies of Form A (obtained from methanol) confirmed that Form A was a disordered, solvated, hydrated crystalline form and therefore represented a group of isostructural solvates.

Form B 10 volumes of water were added to crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide (Form A; 500 mg). The resulting mixture was stirred for 18 hours at 55° C. The solid was cooled to room temperature. The sample was filtered and washed using 5 volumes of water. The solid was dried in an oven at 40° C. and ca. 55 mbar pressure for 24 hours.

Alternatively, 5 volumes of ethyl acetate was added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (250 mg) and the resulting solution was placed in a maturation chamber (switched between room temperature and 50° C. every 4 hours) for 5 days. No solid was recovered and some additions amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide was added until some precipitate appeared. The solution was left to stand at room temperature to allow slow evaporation of the solution. After 6 days the solid was filtered and dried in an oven at 35° C. and ca. 40 mbar for an hour.

In another embodiment, approximately 10 mg of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide (Form A) was transferred to a HPLC vial. A solution was prepared by adding gradually TBME (400 μL) or toluene (800 μL) to the material. After each successive 200 μl addition, the vial was shaken at 50° C. to help dissolution. Once a clear solution was obtained, the vial was left to stand at room temperature with the septum pierced with a needle to allow for slow evaporation of the solvent. After 2 weeks cube-like crystals were obtained from toluene and were submitted for single crystal X-ray diffraction (SCXRD) (see Example 4). The crystalline structure was solved and the form was found to be an unsolvated crystalline form (Form B).

In yet another embodiment, toluene (2 volume), isopropylacetate (2 volume) or MEK (1 volume) was added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The samples were left in screw capped vials at ambient conditions for 3 days. Lids on the samples which showed no precipitation were loosened to allow for slow evaporation of the solvent. After a day, these samples were placed in a maturation chamber, the temperature of which was switched between room temperature and 50° C. every 4 hours. Solid material was isolated.

Form C 4 volumes of isopropanol were added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (160 mg). After 6 days the material was filtered. The sample was placed in an oven at 35° C. and ca. 40 mbar pressure for an hour.

Alternatively, anisole (2 volume), IPA (1 volume) or IPA-water mixture (1 volume) were added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The samples were left in screw capped vials at ambient conditions for 3 days. Lids on the samples which showed no precipitation were loosened to allow for slow evaporation of the solvent. After a day, these samples were placed in a maturation chamber, the temperature of which was switched between room temperature and 50° C. every 4 hours. Solid material was isolated.

Form D 5 volumes of MTBE was added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (200 mg) and the resulting mixture was placed in a maturation chamber (switched between room temperature and 50° C. every 4 hours) for 5 days. The solid obtained was filtered and dried in an oven at 35° C. and ca. 40 mbar pressure for an hour.

Alternatively, MTBE (2 volumes) was added to approximately 65 mg of the amorphous 4-[7-[6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The sample was left in screw capped vial at ambient conditions for 3 days. If the sample showed no precipitation, the lid was loosened to allow for slow evaporation of the solvent. After a day, this sample was placed in a maturation chamber, the temperature of which was switched between room temperature and 50° C. every 4 hours. Solid material was isolated.

Form E

DMSO (1 volume) was added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The sample was left in screw capped vial at ambient conditions for 3 days. If the sample showed no precipitation, the lid was loosened to allow for slow evaporation of the solvent. After a day, this sample was placed in a maturation chamber, the temperature of which was switched between room temperature and 50° C. every 4 hours. Solid material was isolated.

Form F

An acetone/water mixture (1 volume) was added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The sample was left in screw capped vial at ambient conditions for 3 days. If the sample showed no precipitation, the lid was loosened to allow for slow evaporation of the solvent. After a day, this sample was placed in a maturation chamber, the temperature of which was switched between room temperature and 50° C. every 4 hours. Solid material was isolated.

Under ambient conditions, within a month, Form F transformed to Form A.

Form G 4 volumes of 2-methoxyethanol were added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (160 mg). After 6 days the material was filtered. The solid was placed in an oven at 35° C. and ca. 40 mbar pressure for an hour.

Alternatively, 2-methoxyethanol (1 volume) was added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The sample was left in screw capped vial at ambient conditions for 3 days. If the sample showed no precipitation, the lid was loosened to allow for slow evaporation of the solvent. After a day, this sample was placed in a maturation chamber, the temperature of which was switched between room temperature and 50° C. every 4 hours. Solid material was isolated.

Form H

Ethyl acetate (2 volumes) was added to approximately 65 mg of the amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide. A minimum amount of solvent was added just to wet the material (visually this meant softening of the amorphous solid, referred to as collapse). The sample was left in screw capped vial at ambient conditions for 3 days. If the sample showed no precipitation, the lid was loosened to allow for slow evaporation of the solvent. After a day, these samples were placed in a maturation chamber, the temperature of which was switched between room temperature and 50° C. every 4 hours. Solid material was isolated.

Form I 2 volumes of DMSO were added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (150 mg). After 6 days, two lumps of material were obtained— one yellow and the other white colored. The yellow colored material was Form E and the white colored material exhibited a new XRPD. The white colored material was designated as Form I.

Form J 1.9 volumes of acetone and 0.1 volumes of water were added to amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide (200 mg). The lid was left loose and after 6 days the material was found to be completed dry. The resulting material was designated as Form J.

Example 2: Preparation of Amorphous 4-[7-(6-cyano-5-trifluoromethylpyridin-3-yl)-8-oxo-6-thioxo-5,7-diazaspiro[3.4]oct-5-yl]-2-fluoro-N-methylbenzamide 10 Volumes of dichloromethane was added to crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide followed by sonication at 48° C. to provide a clear solution. The resulting solution was rotary evaporated for an hour leading to complete amorphisation of the material (as verified by XRPD analysis).

Example 3: X-Ray Powder Diffraction (XRPD)

X-Ray powder diffraction patterns were collected on a Bruker AXS C2 GADDS or a Bruker AXS D8 Advance diffractometer.

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v 9.0.0.2 or v 13.0.0.2.

Samples run under ambient conditions were prepared as flat plate specimens using powder as received without grinding. Approximately 1-2 mg of the sample was lightly pressed on a glass slide to obtain a flat surface.

Samples run under non-ambient conditions were mounted on a silicon wafer with heat-conducting compound. The sample was then heated to the appropriate temperature at ca.10° C. min$^{-1}$ and subsequently held isothermally for ca 1 minute before data collection was initiated.

Bruker AXS D8 Advance

X-Ray Powder Diffraction patterns were collected on a Bruker D8 diffractometer using Cu Kα radiation (40 kV, 40 mA), 0-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analyzed and presented using Diffrac Plus EVA v 11,0.0.2 or v 13.0.0.2. Samples were run under ambient conditions as flat plate specimens using powder. Approximately 20 mg of the sample was gently packed into a cavity cut into polished, zero-background (510) silicon wafer. The sample was rotated in its own plane during analysis. The details of the data collection are:

Angular range: 2 to 42° 2θ
Step size: 0.05° 2θ
Collection time: 0.5 s·step$^{-1}$ Form A The X-Ray powder diffraction pattern for Form A is displayed in FIG. 1. Characteristic peaks include 4.8±0.1° 2-Theta, 7.1±0.1° 2-Theta, 14.2±0.1° 2-Theta, 16.3±0.1° 2-Theta, 20.1±0.1° 2-Theta.

Form B

The X-Ray powder diffraction pattern for Form B is displayed in FIG. 2. Characteristic peaks include 12.1±0.1° 2-Theta, 16.0±0.1° 2-Theta, 16.7±0.1° 2-Theta, 20.1±0.1° 2-Theta, 20.3±0.1° 2-Theta.

Form C

The X-Ray powder diffraction pattern for Form C is displayed in FIG. 3. Characteristic peaks include 4.3±0.1° 2-Theta, 6.9±0.1° 2-Theta, 9.1±0.1° 2-Theta, 10.6±0.1° 2-Theta, 13.8±0.1° 2-Theta, 26.4±0.1° 2-Theta.

Form D

The X-Ray powder diffraction pattern for Form D is displayed in FIG. 4. Characteristic peaks include 6.3±0.1° 2-Theta, 13.9±0.1° 2-Theta, 16.4±0.1° 2-Theta, 17.0±0.1° 2-Theta, 23.7±0.1° 2-Theta, 24.8±0.1° 2-Theta.

Form E

The X-Ray powder diffraction pattern for Form E is displayed in FIG. 5. Characteristic peaks include 7.2±0.1° 2-Theta, 11.8±0.1° 2-Theta, 16.1±0.1° 2-Theta, 20.5±0.1° 2-Theta, 23.0±0.1° 2-Theta, 25.2±0.1° 2-Theta. Variable temperature XRPD showed transformation of Form E to Form A to Form B.

Form F

The X-Ray powder diffraction pattern for Form F is displayed in FIG. 6. Characteristic peaks include 4.6±0.1° 2-Theta, 6.1±0.1° 2-Theta, 14.3±0.1° 2-Theta, 21.6±0.1° 2-Theta, 22.4±0.1° 2-Theta, 23.3±0.1° 2-Theta, 25.5±0.1° 2-Theta.

Form G

The X-Ray powder diffraction pattern for Form G is displayed in FIG. 7. Characteristic peaks include 7.0±0.1° 2-Theta, 10.3±0.1° 2-Theta, 14.1±0.1° 2-Theta, 15.2±0.1° 2-Theta, 23.6±0.1° 2-Theta.

Form H

The X-Ray powder diffraction pattern for Form H is displayed in FIG. 8. Characteristic peaks include 8.0±0.1° 2-Theta, 14.7±0.1° 2-Theta, 15.9±0.1° 2-Theta, 18.2±0.1° 2-Theta, 25.7±0.1° 2-Theta, 26.7±0.1° 2-Theta.

Form I

The X-Ray powder diffraction pattern for Form I is displayed in FIG. 9. Characteristic peaks include 7.7±0.1° 2-Theta, 10.4±0.1° 2-Theta, 11.6±0.1° 2-Theta, 17.0±0.1° 2-Theta, 20.0±0.1° 2-Theta, 20.6±0.1° 2-Theta.

Form J

The X-Ray powder diffraction pattern for Form J is displayed in FIG. 10. Characteristic peaks include 8.6±0.1° 2-Theta, 19.3±0.1° 2-Theta, 20.8±0.1° 2-Theta, 24.3±0.1° 2-Theta, 27.6±0.1° 2-Theta.

Example 4: Single Crystal X-Ray Diffraction (SCXRD)

Single crystal X-ray diffraction data was collected on an Oxford Diffraction Supernova Dual Source, Cu at Zero, Atlas CCD diffractometer equipped with an Oxford Cryosystems Cryostream/Cobra cooling device. The data was collected using CuKα/MoKα radiation. Structures were typically solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Form A

Form A is characterized by unit cell unit cell parameters approximately equal to the following at a temperature of approximately −173° C.:

TABLE 1

| Single Crystal Structure of Form A | | | | | |
|---|---|---|---|---|---|
| Molecular formula | | $C_{21}H_{15}F_4N_5O_2S_1$ | | | |
| Molecular weight | | 485.5 | | | |
| Crystal system | | Orthorhombic | | | |
| Space group | P2(1)2(1)2 | a | 16.3429(3) Å | α | 90° |
| | | b | 37.7298(7) Å | β | 90° |
| | | c | 7.23410(10) Å | γ | 90° |
| V | | 4460.65(13) Å3 | | | |
| Z | | 8 | | | |
| Dc | | 1.446 g · cm$^{-1}$ | | | |
| μ | | 0.207 mm$^{-1}$ | | | |
| Source, λ | | Mo—K(alpha), 0.71073 Å | | | |
| F(000) | | 2016 | | | |
| T | | 100(2) K | | | |
| Crystal | | Colourless block, 0.25 × 0.2 × 0.1 mm | | | |
| Data truncated to | | 0.80 Å | | | |
| θmax | | 26.37° | | | |
| Completeness | | 99.4% | | | |
| Reflections | | 67442 | | | |
| Unique reflections | | 9056 | | | |
| Rint | | 0.0425 | | | |

The structure solution was obtained by direct methods, full-matrix least-squares refinement on $F^2$ with weighting $w^{-1}=\sigma2(F_o^2)+(0.1070P)^2+(6.5000P)$, where $P=(F_o^2+2F_c^2)/3$, anisotropic displacement parameters, empirical absorption correction using spherical harmonics, implemented in SCALE3 ABSPACK scaling algorithm Final $wR^2=\{\Sigma[w(F_o^2-F_c^2)^2]/\sigma[w(F_o^2)^2]^{1/2}\}=0.1814$ for all data, conventional $R_1=0.0652$ on F values of 7570 reflections with $F_o>4\sigma(F_o)$, S=1.005 for all data and 642 parameters. Final Δ/σ (max)0.004, Δ/σ (mean), 0.000. Final difference map between +1.158 and −0.443 e Å$^{-3}$.

A simulated XRPD obtained from the single crystal data for Form A matched the experimental XRPD.

The single crystal XRD analysis confirmed that Form A is a disordered, solvated, hydrated crystalline form. Since Form A was obtained from different solvents, it can be concluded that Form A represents a group of isostructural solvates.

Form B

Form B is characterized by unit cell unit cell parameters approximately equal to the following at a temperature of approximately −173° C.:

TABLE 2

| Single Crystal Structure of Form B | | | | | |
|---|---|---|---|---|---|
| Molecular formula | | $C_{21}H_{15}F_4N_5O_2S$ | | | |
| Molecular weight | | 477.44 | | | |
| Crystal system | | Monoclinic | | | |
| Space group | P2$_1$/c | a | 17.7796(4) Å | α | 90° |
| | | b | 12.9832(3) Å | β | 100.897(2)° |
| | | c | 18.4740(4) Å | γ | 90° |
| V | | 4187.57(16) Å$^3$ | | | |
| Z | | 8 | | | |
| Dc | | 1.515 g · cm$^{-1}$ | | | |
| μ | | 0.22 mm$^{-1}$ | | | |
| Source, λ | | Mo—K(alpha), 0.71073 Å | | | |
| F(000) | | 1952 | | | |
| T | | 100(2) K | | | |
| Crystal | | colourless prism, 0.23 × 0.20 × 0.05 mm,, 0.3 × 0.3 × 0.2 mm | | | |
| Data truncated to | | 0.80 Å | | | |
| θmax | | 26.37° | | | |
| Completeness | | 99.6% | | | |
| Reflections | | 27616 | | | |
| Unique reflections | | 8527 | | | |
| Rint | | 0.0458 | | | |

The structure solution was obtained by direct methods, full-matrix least-squares refinement on $F^2$ with weighting $w^1=\sigma2(F_o^2)+(0.0425P)^2+(0.0000P)$, where $P=(F_o^2+2F_c^2)/3$, anisotropic displacement parameters, empirical absorption correction using spherical harmonics, implemented in SCALE3 ABSPACK scaling algorithm Final wR$^2$={Σ[w(F$_o^2$-F$_c^2$)$^2$]/Σ[w(F$_o^2$)$^2$]$^{1/2}$}=0.0941 for all data, conventional R$_1$=0.0404 on F values of 5767 reflections with F$_o$>4σ(F$_o$), S=1.005 for all data and 613 parameters. Final Δ/σ (max) 0.001, Δ/σ (mean), 0.000. Final difference map between +0.76 and −0.603 e Å$^{-3}$.

A simulated XRPD obtained from the single crystal data for Form B matched the experimental XRPD.

The single crystal XRD analysis confirmed that Form B is unsolvated.

Form E

Form E is characterized by unit cell unit cell parameters approximately equal to the following at a temperature of approximately −173° C.:

TABLE 3

Single Crystal Structure of Form E

| | | | | |
|---|---|---|---|---|
| Molecular formula | | C$_{23}$H$_{21}$F$_4$N$_5$O$_3$S$_2$ | | |
| Molecular weight | | 555.57 | | |
| Crystal system | | Orthorhombic | | |
| Space group | P$_{na}$2$_1$ | a 8.43080(10) Å | α | 90° |
| | | b 17.1685(3) Å | β | 90° |
| | | c 17.4276(3) Å | γ | 90° |
| V | | 2522.54(7) Å$^3$ | | |
| Z | | 4 | | |
| Dc | | 1.463 g · cm$^{-1}$ | | |
| μ | | 2.504 mm$^{-1}$ | | |
| Source, λ | | Cu Kα, 1.54178 Å | | |
| F(000) | | 1144 | | |
| T | | 100(2) K | | |
| Crystal | | colourless prism, 0.23 × 0.20 × 0.05 mm,, 0.3 × 0.2 × 0.07 mm | | |
| Data truncated to | | 0.80 Å | | |
| θmax | | 74.48° | | |
| Completeness | | 99.6% | | |
| Reflections | | 11318 | | |
| Unique reflections | | 4424 | | |
| Rint | | 0.019 | | |

The structure solution was obtained by direct methods, full-matrix least-squares refinement on F$^2$ with weighting w$^{-1}$=σ2(F$_o^2$)+(0.1120P)$^2$+(1.1000P), where P=(F$_o^2$+2F$_c^2$)/3, anisotropic displacement parameters, empirical absorption correction using spherical harmonics, implemented in SCALE3 ABSPACK scaling algorithm Final wR$^2$={Σ[w(F$_o^2$-F$_c^2$)$^2$]/Σ[w(F$_o^2$)$^2$]$^{1/2}$}=0.1442 for all data, conventional R$_1$=0.0492 on F values of 4257 reflections with F$_o$>4σ(F$_o$), S=1.01 for all data and 342 parameters. Final Δ/σ (max) 0.000, Δ/σ (mean), 0.000. Final difference map between +1.923 and −0.527 e Å$^{-3}$.

A simulated XRPD obtained from the single crystal data for Form E matched the experimental XRPD.

The single crystal XRD (SCXRD) studies of Form E confirmed that it was a 1:1 DMSO solvate.

Form G

Form G is characterized by unit cell unit cell parameters approximately equal to the following at a temperature of approximately −173° C.:

TABLE 4

Single Crystal Structure of Form G

| | | | | |
|---|---|---|---|---|
| Molecular formula | | C$_{24}$H$_{23}$F$_4$N$_5$O$_4$S | | |
| Molecular weight | | 553.53 | | |
| Crystal system | | Monoclinic | | |
| Space group | Cc | a 18.613(2) Å | α | 90° |
| | | b 16.9728(14) Å | β | 91.328(8)° |

TABLE 4-continued

Single Crystal Structure of Form G

| | | | | |
|---|---|---|---|---|
| | | c 7.8214(7) Å | γ | 90° |
| V | | 2470.2(4)Å$^3$ | | |
| Z | | 4 | | |
| Dc | | 1.488 g · cm$^{-1}$ | | |
| μ | | 0.203 mm$^{-1}$ | | |
| Source, λ | | Mo—K(alpha), 0.71073 Å | | |
| F(000) | | 1144 | | |
| T | | 100(2) K | | |
| Crystal | | colourless prism, 0.23 × 0.20 × 0.05 mm,, 0.5 × 0.1 × 0.1 mm | | |
| Data truncated to | | 0.80 Å | | |
| θmax | | 26.37° | | |
| Completeness | | 99.6% | | |
| Reflections | | 11648 | | |
| Unique reflections | | 4309 | | |
| Rint | | 0.0565 | | |

The structure solution was obtained by direct methods, full-matrix least-squares refinement on F$^2$ with weighting w$^{-1}$=σ2(F$_o^2$)+(0.0790P)$^2$+(0.0000P), where P=(F$_o^2$+2F$_c^2$)/3, anisotropic displacement parameters, empirical absorption correction using spherical harmonics, implemented in SCALE3 ABSPACK scaling algorithm Final wR$^2$={Σ[w(F$_o^2$-F$_c^2$)$^2$]/Σ[w(F$_o^2$)$^2$]$^{1/2}$}=0.114 for all data, conventional R$_1$=0.0442 on F values of 3799 reflections with F$_o$>4σ(F$_o$), S=1.005 for all data and 353 parameters. Final Δ/σ (max) 0.000, Δ/σ (mean), 0.000. Final difference map between +0.502 and −0.401 e Å$^{-3}$.

A simulated XRPD obtained from the single crystal data for Form G matched the experimental XRPD.

The single crystal XRD studies (SCXRD) of Form G confirmed that it was a 1:1 2-methoxyethanol solvate.

Example 5: Differential Scanning Calorimetry (DSC) and Thermogravimetric Analysis (TGA)

DSC data were collected on a TA Instruments Q2000 or Mettler DSC 823e.

In some cases, DSC data were collected on a TA Instruments Q2000 equipped with a 50 position autosampler. The calibration for thermal capacity was carried out using sapphire and the calibration for energy and temperature was carried out using certified indium. Typically 0.5-3 mg of each sample, in a pin-holed aluminium pan, was heated at 10° C.·min$^{-1}$ from 25° C. to 350° C. A purge of dry nitrogen at 50 ml·min$^{-1}$ was maintained over the sample. Modulated temperature DSC was carried out using an underlying heating rate of 2° C.·min-1 and temperature modulation parameters of ±0.2° C.·min$^{-1}$ and 40 seconds. The instrument control software was Advantage for Q Series v2.8.0.392 and Thermal Advantage v4.8.3 and the data were analysed using Universal Analysis v4.3A.

In other cases, DSC data were collected on a Mettler DSC 823e equipped with a 34 position auto-sampler. The instrument was calibrated for energy and temperature using certified indium. Typically 0.5-3 mg of each sample, in a pin-holed aluminium pan, was heated at 10° C.·min$^{-1}$ from 25° C. to 350° C. A nitrogen purge at 50 ml·min$^{-1}$ was maintained over the sample. The instrument control and data analysis software was STARe v9.20.

TGA data were collected on a TA Instruments Q500 or Mettler TGA/SDTA 851e.

In some cases, TGA data were collected on a TA Instruments Q500 TGA, equipped with a 16 position autosampler. The instrument was temperature calibrated using certified Alumel. Typically 5-30 mg of each sample was loaded onto a pre-tared platinum crucible and aluminium DSC pan, and was heated at 10° C.·min$^{-1}$ from ambient temperature to 350° C. A nitrogen purge at 60 ml·min-1 was maintained over the sample. The instrument control software was Advantage for Q Series v2.8.0.392 and Thermal Advantage v4.8.3.

In other cases, TGA data were collected on a Mettler TGA/SDTA 851e equipped with a 34 position autosampler. The instrument was temperature calibrated using certified indium. Typically 5-30 mg of each sample was loaded onto a pre-weighed aluminium crucible and was heated at 10° C.·min$^{-1}$ from ambient temperature to 350° C. A nitrogen purge at 50 ml·min$^{-1}$ was maintained over the sample. The instrument control and data analysis software was STARe v9.20.

Form A

The single crystal XRD analysis confirmed that Form A is a disordered, solvated, hydrated crystalline form. A sample of the ethanol solvate showed an endotherm having an onset at about 108-120° C. and a peak at about 133-135° C. A representative DSC thermogram is shown in FIG. 19. In some embodiments, variable temperature XRPD experiments showed Form A to become amorphous above about 120° C. followed by a recrystallization to Form B at about 175° C., which subsequently melted at about 194° C.

Form B

A sample of Form B was analyzed by TGA and DSC and the thermograms are shown in FIG. 11. TGA showed no weight loss above the decomposition temperature and DSC showed a sharp melting endotherm with an onset temperature at about 194° C.

Form C

A sample of Form C (from isopropanol) was analyzed by TGA and DSC and the thermograms are shown in FIG. 12. An endotherm with an onset temperature at about 118° C. was observed. A small endotherm with an onset temperature at about 193° C. was also observed. The weight loss observed in the TGA experiment matched the temperature range in which the Form lost crystallinity by VT-XRPD suggesting that Form C was not unsolvated. 0.45 equivalents of isopropanol was observed by $^{1}$H NMR and 0.49 equivalents of isopropanol was calculated from the weight loss in TGA. Form C obtained from isopropanol is an isopropanol solvate.

Form D

A sample of Form D was analyzed by TGA and DSC, and the thermograms are shown in FIG. 13. An endotherm with an onset temperature at about 122° C. was observed. A smaller second endotherm with an onset temperature at about 192° C. was also observed.

The weight loss observed in the TGA experiment matched the temperature range in which the Form lost crystallinity by VT-XRPD suggesting that Form D was not unsolvated. 0.26 equivalents of MTBE was observed by $^{1}$H NMR, and 0.26 equivalents of MTBE was calculated from the weight loss in TGA. Form D obtained from MTBE is a MTBE solvate.

Form E

A sample of Form E was analyzed by TGA and DSC, and the thermograms are shown in FIG. 14. A main endotherm having an onset temperature at about 116° C. was observed. A relatively small endotherm having an onset temperature at about 140° C. was also observed. On heating at 10° C./min in a DSC pan, an endotherm at 140° C. was observed. VT-XRPD showed transformation of Form E to Form A to Form B.

Form F

A sample of Form F was analyzed by TGA and DSC, and the thermograms are shown in FIG. 15. A main endotherm having an onset temperature at about 113° C. was observed. A relatively small endotherm having an onset temperature at about 193° C. was also observed.

Form G

A sample of Form G was analyzed by DSC, and the thermogram is shown in FIG. 16. A main endotherm having an onset temperature at about at 101° C. was observed. A relatively small endotherm having an onset temperature at about 190° C. was also observed.

Form H

A sample of Form H was analyzed by TGA and DSC, and the thermograms are shown in FIG. 17. The TGA thermogram showed no weight loss below the decomposition temperature. The DSC thermogram showed a sharp melting endotherm with an onset temperature of 173° C., and a relatively smaller endotherm with an onset temperature of 193° C. Based on these observations and the $^{1}$H NMR spectrum (i.e. no significant amount of solvent observed), Form H is unsolvated.

Form J

A sample of Form J was analyzed by TGA and DSC and the thermograms are shown in FIG. 18. An endotherm having an onset temperature at about 104° C. was observed. An endotherm having an onset temperature at about 193° C. was also observed. The weight loss observed in the TGA experiment matched the temperature range in which Form J lost crystallinity by VT-XRPD suggesting that Form J was not unsolvated. 0.45 equivalents of acetone was observed by $^{1}$H NMR, and 0.46 equivalents of acetone was calculated from the weight loss in TGA. Form J obtained from an acetone/water mixture is an acetone solvate.

Example 6: Gravimetric Vapour Sorption (GVS)

Sorption isotherms were obtained using a SMS DVS Intrinsic moisture sorption analyser, controlled by SMS Analysis Suite software. The sample temperature was maintained at 25° C. by the instrument controls. The humidity was controlled by mixing streams of dry and wet nitrogen, with a total flow rate of 200 ml·min$^{-1}$ The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range.

TABLE 5

Method Parameters for SMS DVS Intrinsic Experiments

| Parameters | Values |
|---|---|
| Adsorption - Scan 1 | 40-90 |
| Desorption/Adsorption - Scan 2 | 90-0, 0-40 |
| Intervals (% RH) | 10 |
| Number of Scans | 4 |
| Flow rate (ml · min$^{-1}$) | 200 |
| Temperature (° C.) | 25 |

TABLE 5-continued

| Method Parameters for SMS DVS Intrinsic Experiments | |
|---|---|
| Parameters | Values |
| Stability (° C. min$^{-1}$) | 0.2 |
| Sorption Time (hours) | 6 hour time out |

The sample was recovered after completion of the isotherm and re-analyzed by XRPD.

Form A

Form A solvates were stable at 40° C. and 75% RH for at least a week.

Form B

The GVS isotherms of Form B at 25° C. showed that the uptake of water by Form B at 90% RH was less than 0.2%; therefore, Form B was not hygroscopic. No change in the XRPD pattern of the material after GVS analysis was observed suggesting that Form B was stable under the GVS conditions.

No difference in the XRPD patterns of Form B before and after storage at 25° C. and 92% RH for 12 days was observed suggesting that Form B was stable under these conditions.

Form B was stable at 40° C. and 75% RH for at least a week.

Form C

Form C was stable at 40° C. and 75% RH for at least a week.

Form D

Form D was stable at 40° C. and 75% RH for at least a week.

Form E

Under the GVS conditions, Form E transformed to Form A.

A sample of Form E was laid on a glass slide then placed in a box maintained at 92% RH/25° C. Under these conditions, after a week Form E transformed to Form A and a small amount of Form B.

Form E transformed to Form A at 40° C. and 75% RH within a week.

Form F

Form F transformed to Form A at 40° C. and 75% RH within a week.

Form G

Form G was stable at 40° C. and 75% RH for at least a week.

Form H

Form H was stable at 40° C. and 75% RH for at least a week.

Form I

A sample of Form I was laid on a glass slide then placed in a box maintained at 92% RH/25° C. Under these conditions, after a week Form I transformed to Form B.

Form J

A sample of Form J was laid on a glass slide then placed in a box maintained at 92% RH/25° C. Under these conditions, after a week Form J transformed to Form B.

Example 7: Water Determination by Karl Fischer Titration (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approximately 10 mg of sample was used per titration and duplicate determinations were made.

In some embodiments, the water content for Form A was observed to be 2.5% (w/w).

In some embodiments, the water content for Form C was observed to be 0.4% (w/w).

In some embodiments, the water content for Form D was observed to be 0.3% (w/w).

In some embodiments, the water content for Form J was observed to be 0.3% (w/w).

Example 8: Thermodynamic Aqueous Solubility

Aqueous solubility was determined by suspending sufficient compound in water to give a maximum final concentration of $\geq 20$ mg·ml$^{-1}$ of the parent free-form of the compound. The suspension was equilibrated at 25° C. for 24 hours then the pH was measured. The suspension was then filtered through a glass fibre C filter into a 96 well plate unless stated otherwise. The filtrate was then diluted by a factor of 101. Quantitation was by HPLC with reference to a standard solution of approximately 0.1 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

TABLE 6

| HPLC Method Parameters for Solubility Measurements | | |
|---|---|---|
| Type of method: | Reverse phase with gradient elution | |
| Column: | Phenomenex Luna, C18 (2) 5 µm 50 × 4.6 mm | |
| Column Temperature (° C.): | 25 | |
| Standard Injections (µl): | 1, 2, 3, 5, 7, 10 | |
| Test Injections (µl): | 1, 2, 3, 10, 20, 50 | |
| Detection: Wavelength, Bandwidth (nm): | 260, 80 | |
| Flow Rate (ml.min$^{-1}$): | 2 | |
| Phase A: | 0.1% TFA in water | |
| Phase B: | 0.085% TFA in acetonitrile | |
| | Time (min) | % Phase A | % Phase B |
| Timetable: | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

TABLE 7

| Solubility results | |
|---|---|
| Form | Aqueous Solubility (mg/mL) |
| A | 0.01 |
| B | 0.004 |

Example 9: Chemical Purity Determination

Purity analysis was performed by HPLC on an Agilent HP1100 series system equipped with a diode array detector and using ChemStation software vB.02.01-SR1.

TABLE 8

| HPLC Method Parameters for Chemical Purity Determinations | |
|---|---|
| Sample Preparation: | 0.5 mg/ml in acetonitrile:water 1:1 (unless otherwise stated) |
| Column: | Supelco Ascentis Express C18, 100 × 4.6 mm, 2.7 μm |
| Column Temperature (° C.): | 25 |
| Injection (μl): | 5 (unless otherwise stated) |
| Detection: | |
| Wavelength, Bandwidth (nm): | 255, 90 |
| Flow Rate (ml · min−1): | 2.0 |
| Phase A: | 0.1% TFA in water |
| Phase B: | 0.085% TFA in acetonitrile |

| | Time (min) | % Phase A | % Phase B |
|---|---|---|---|
| Timetable: | 0 | 95 | 5 |
| | 6 | 5 | 95 |
| | 6.2 | 95 | 5 |
| | 8 | 95 | 5 |

Samples of 4-[7-(6-cyano-5-trifluoromethylpyridin-3-yl)-8-oxo-6-thioxo-5,7-diazaspiro[3.4]oct-5-yl]-2-fluoro-N-methylbenzamide were found to be greater than 95% pure. In some embodiments, samples of 4-[7-(6-cyano-5-trifluoromethylpyridin-3-yl)-8-oxo-6-thioxo-5,7-diazaspiro[3.4]oct-5-yl]-2-fluoro-N-methylbenzamide were found to be greater than 95% pure, greater than 96% pure, greater than 97% pure, greater than 98% pure, or greater than 99% pure.

Example 10: Pharmaceutical Composition

Capsule Formulation

In one embodiment, capsule formulations of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide for administration to humans are prepared with the following ingredients:

TABLE 9

| Components of Capsule Formulation | | | |
|---|---|---|---|
| Component | Function | Quantity per Size 4 Capsule | Quantity per Size 1 Capsule |
| crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide | Active | 5 to 100 mg | 50 to 500 mg |
| Hypromellose, USP | Capsule Shell | 1 capsule | 1 capsule |

The process to prepare crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide in a capsule is as follows: Weigh the required amount of crystalline 4-[7-(6-cyano-5-trifluoromethylpyridin-3-yl)-8-oxo-6-thioxo-5,7-diazaspiro[3.4]oct-5-yl]-2-fluoro-N-methylbenzamide, add into the appropriate size capsule, and close capsule.

In some embodiments, the capsules are stored at 25° C. for up to 48 hours.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A crystalline Form A of 4-[7-(6-cyano-5-trifluoromethylpyridin-3-yl)-8-oxo-6-thioxo-5,7-diazaspiro[3.4]oct-5-yl]-2-fluoro-N-methylbenzamide that exhibits:
   (a) an X-ray powder diffraction (XRPD) pattern with characteristic peaks at 4.8±0.1° 2-Theta, 7.1±0.1° 2-Theta, 14.2±0.1° 2-Theta, 16.3±0.1° 2-Theta, and 20.1±0.1° 2-Theta; or
   (b) unit cell parameters substantially equal to the following at −173° C.:

| Crystal system | | Orthorhombic | | | |
|---|---|---|---|---|---|
| Space group | P2(1)2(1)2 | a | 16.3429(3) Å | α | 90° |
| | | b | 37.7298(7) Å | β | 90° |
| | | c | 7.23410(10) Å | γ | 90° |
| V | | 4460.65(13) Å3 | | | |
| Z | | 8 | | | |
| Dc | | 1.446 g · cm$^{-1}$ | | | | and optionally:
   (c) a DSC thermogram with an endotherm having an onset temperature at about 108-120° C. and a peak at about 133-135° C.

2. The crystalline Form A of claim 1 that exhibits an X-ray powder diffraction (XRPD) pattern with characteristic peaks at 4.8±0.1° 2-Theta, 7.1±0.1° 2-Theta, 14.2±0.1° 2-Theta, 16.3±0.1° 2-Theta, and 20.1±0.1° 2-Theta.

3. The crystalline Form A of claim 1, wherein the crystalline form exhibits an X-Ray powder diffraction (XRPD) pattern substantially the same as shown in FIG. 1.

4. The crystalline Form A of claim 1, wherein the crystalline form has unit cell parameters substantially equal to the following at −173° C.:

| Crystal system | | Orthorhombic | | | |
|---|---|---|---|---|---|
| Space group | P2(1)2(1)2 | a | 16.3429(3) Å | α | 90° |
| | | b | 37.7298(7) Å | β | 90° |
| | | c | 7.23410(10) Å | γ | 90° |
| V | | 4460.65(13) Å3 | | | |
| Z | | 8 | | | |
| Dc | | 1.446 g · cm$^{-1}$. | | | |

5. The crystalline Form A of claim 1, wherein the crystalline form exhibits substantially the same X-ray powder diffraction (XRPD) pattern post storage at 40° C. and 75% RH for at least a week.

6. The crystalline Form A of claim 1, wherein the crystalline form exhibits a DSC thermogram with an endotherm having an onset temperature at about 108-120° C. and a peak at about 133-135° C.

7. The crystalline Form A of claim 1, wherein the crystalline form exhibits a DSC thermogram substantially similar to the one set forth in FIG. 19.

8. The crystalline Form A of claim 1, wherein the crystalline form is characterized as exhibiting properties (a), (b), and (c).

9. The crystalline Form A of claim 1, wherein the crystalline form was obtained from ethanol, tetrahydrofuran (THF), dichloromethane, acetone, methanol, nitromethane, water, THF-water mixture, or dioxane-water mixture.

10. The crystalline Form A of claim 1, wherein the crystalline form was obtained from ethanol.

11. The crystalline Form A of claim 1, wherein the crystalline form is solvated by ethanol, acetone, or methanol.

12. The crystalline Form A of claim 1, wherein the crystalline form is an ethanol solvate.

13. The crystalline Form A of claim 1, wherein the crystalline form is a hydrate.

14. The crystalline Form A of claim 1, wherein the crystalline form is a solvated hydrate.

15. A pharmaceutical composition comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and at least one additional ingredient selected from pharmaceutically acceptable carriers, diluents and excipients, in which the 4-[7-(6-cyano-5-trifluoromethylpyridin-3-yl)-8-oxo-6-thioxo-5,7-diazaspiro[3.4]oct-5-yl]-2-fluoro-N-methylbenzamide in the composition comprises the crystalline Form A of claim 1.

16. The pharmaceutical composition according to claim 15, wherein the pharmaceutical composition is in a form formulated for oral administration to a mammal.

17. The pharmaceutical composition according to claim 15, wherein the pharmaceutical composition is in an oral solid dosage form.

18. The pharmaceutical composition according to claim 15, wherein the pharmaceutical composition comprises about 0.5 mg to about 1000 mg of the crystalline Form A of 4-[7-(6-cyano-5-trifluoromethylpyridin-3-yl)-8-oxo-6-thioxo-5,7-diazaspiro[3.4]oct-5-yl]-2-fluoro-N-methylbenzamide.

19. A method of treating prostate cancer in a mammal comprising administering the crystalline Form A of 4-[7-(6-cyano-5-trifluoromethylpyridin-3-yl)-8-oxo-6-thioxo-5,7-diazaspiro[3.4]oct-5-yl]-2-fluoro-N-methylbenzamide according to claim 1 to a mammal in need of such treatment.

20. A method of treating prostate cancer in a mammal comprising administering the pharmaceutical composition according to claim 15 to a mammal in need of such treatment.

21. The method of claim 19, wherein the prostate cancer is hormone sensitive prostate cancer or hormone refractory prostate cancer.

* * * * *

UNITED STATES PATENT AND TRADEMARK OFFICE
CERTIFICATE OF CORRECTION

| | | |
|---|---|---|
| PATENT NO. | : 9,994,545 B2 | Page 1 of 1 |
| APPLICATION NO. | : 15/262522 | |
| DATED | : June 12, 2018 | |
| INVENTOR(S) | : Anna Dilhas et al. | |

It is certified that error appears in the above-identified patent and that said Letters Patent is hereby corrected as shown below:

On the Title Page

Item (72) Inventors:
Delete "Mark R. Herbert, San Diego, CA (US)" and "Nicholas D. Smith, San Diego, CA (US)"

Signed and Sealed this
Twelfth Day of September, 2023

Katherine Kelly Vidal
*Director of the United States Patent and Trademark Office*